United States Patent
Sullivan et al.

(10) Patent No.: US 11,536,707 B2
(45) Date of Patent: Dec. 27, 2022

(54) SYSTEMS AND METHODS FOR INTEGRATION OF MICROFLUIDIC TEAR COLLECTION AND LATERAL FLOW ANALYSIS OF ANALYTES OF INTEREST

(71) Applicant: Tearlab Research, Inc., San Diego, CA (US)

(72) Inventors: Benjamin Sullivan, San Diego, CA (US); Steve Zmina, San Diego, CA (US); Melissa Lee, San Diego, CA (US); Brandon Westerberg, San Diego, CA (US); Matthew Daniel Solomon, Scoresby (AU); Christian Potzner, Scoresby (AU); Sebastiaan Garst, Scoresby (AU); Matthew Springer, Scoresby (AU); Jason Hayes, Scoresby (AU); Peter Munster, Scoresby (AU); Erol Craig Harvey, Scoresby (AU); Michael Wilkinson, Scoresby (AU); Joanna Slowinska, Scoresby (AU); Derek Lee, Scoresby (AU); Peter Van Ruijven, Scoresby (AU)

(73) Assignee: TEARLAB RESEARCH, INC., San Diego, CA (US)

( * ) Notice: Subject to any disclaimer, the term of this patent is extended or adjusted under 35 U.S.C. 154(b) by 455 days.

(21) Appl. No.: 15/503,823

(22) PCT Filed: Sep. 23, 2015

(86) PCT No.: PCT/US2015/051772
§ 371 (c)(1),
(2) Date: Feb. 14, 2017

(87) PCT Pub. No.: WO2016/049221
PCT Pub. Date: Mar. 31, 2016

(65) Prior Publication Data
US 2017/0248573 A1    Aug. 31, 2017

Related U.S. Application Data

(60) Provisional application No. 62/053,923, filed on Sep. 23, 2014.

(51) Int. Cl.
*G01N 33/543* (2006.01)
*G01N 33/487* (2006.01)
(Continued)

(52) U.S. Cl.
CPC .......... *G01N 33/487* (2013.01); *B01L 3/5027* (2013.01); *B01L 3/502715* (2013.01);
(Continued)

(58) Field of Classification Search
CPC ..... B01L 2200/0605; B01L 2200/0642; B01L 2200/0647; B01L 2200/0684;
(Continued)

(56) References Cited

U.S. PATENT DOCUMENTS 4,028,931 A    6/1977   Bisera et al.
4,123,701 A    10/1978  Josefsen et al.
(Continued)

FOREIGN PATENT DOCUMENTS

CA    2682070 A1    10/2008
DE    3414866 A1    10/1985
(Continued)

OTHER PUBLICATIONS

He et al. Automating fluid delivery in a capillary microfluidic device using low-voltage electrowetting valves. Microfluid Nanfluid 16:879-886 (2014).
(Continued)

*Primary Examiner* — Melanie Brown
(74) *Attorney, Agent, or Firm* — Wilson Sonsini Goodrich & Rosati

(57) ABSTRACT

Systems, methods, and devices for analyzing small volumes of fluidic samples, as a non-limiting example, less than twenty microliters are provided. The devices are configured to make a first sample reading, for example, measure an energy property of the fluid sample, for example, osmolality, make a second sample reading, for example, detecting the presence or concentration of one or more analytes in the fluid sample, or make both the first sample reading and the second sample reading, for example, measuring the energy property of the fluid sample as well as detecting the presence or concentration of one or more analytes in the fluid sample.

20 Claims, 11 Drawing Sheets

(51) Int. Cl.
    *G01N 13/04* (2006.01)
    *B01L 3/00* (2006.01)
    *B81B 1/00* (2006.01)
    *G01N 35/10* (2006.01)
    *G01N 35/00* (2006.01)

(52) U.S. Cl.
    CPC ... *B01L 3/502738* (2013.01); *B01L 3/502746* (2013.01); *B01L 3/502761* (2013.01); *B81B 1/00* (2013.01); *G01N 13/04* (2013.01); *G01N 33/54366* (2013.01); *G01N 35/10* (2013.01); *B01L 2200/0605* (2013.01); *B01L 2200/0642* (2013.01); *B01L 2200/0647* (2013.01); *B01L 2200/0684* (2013.01); *B01L 2300/069* (2013.01); *B01L 2300/0672* (2013.01); *B01L 2300/08* (2013.01); *B01L 2300/0838* (2013.01); *B01L 2300/0858* (2013.01); *B01L 2300/161* (2013.01); *B01L 2300/165* (2013.01); *B01L 2400/0688* (2013.01); *B01L 2400/086* (2013.01); *B81B 2201/058* (2013.01); *B81B 2203/0338* (2013.01); *G01N 2035/00237* (2013.01); *G01N 2035/1034* (2013.01)

(58) Field of Classification Search
    CPC ....... B01L 2300/0672; B01L 2300/069; B01L 2300/08; B01L 2300/0838; B01L 2300/0858; B01L 2300/161; B01L 2300/165; B01L 2400/0688; B01L 2400/086; B01L 3/5027; B01L 3/502715; B01L 3/502738; B01L 3/502746; B01L 3/502761; B81B 1/00; B81B 2201/058; B81B 2203/0338; G01N 13/04; G01N 2035/00237; G01N 2035/1034; G01N 33/487; G01N 33/54366; G01N 35/10
    See application file for complete search history.

(56) References Cited

U.S. PATENT DOCUMENTS

| | | | |
|---|---|---|---|
| 4,134,730 A | 1/1979 | Quame |
| 4,150,564 A | 4/1979 | Barlow et al. |
| 4,245,495 A | 1/1981 | Kakiuchi et al. |
| 4,269,197 A | 5/1981 | Gilbard |
| 4,301,412 A | 11/1981 | Hill et al. |
| 4,305,823 A | 12/1981 | Batzer et al. |
| 4,436,094 A | 3/1984 | Cerami |
| 4,448,207 A | 5/1984 | Parrish |
| 4,449,538 A | 5/1984 | Corbitt et al. |
| 4,455,864 A | 6/1984 | Wallner |
| 4,475,556 A | 10/1984 | Reiff |
| 4,587,003 A | 5/1986 | Tantram et al. |
| 4,603,699 A | 8/1986 | Himpens |
| 4,658,833 A | 4/1987 | Stuart |
| 4,706,495 A | 11/1987 | Steudle et al. |
| 4,787,963 A | 11/1988 | MacConnell |
| 4,867,909 A | 9/1989 | Babinec et al. |
| 4,872,956 A | 10/1989 | Kotani et al. |
| 4,951,683 A | 8/1990 | Davis |
| 4,996,993 A | 3/1991 | York |
| 5,005,403 A | 4/1991 | Steudle et al. |
| 5,112,622 A | 5/1992 | Kopp |
| 5,132,012 A | 7/1992 | Miura et al. |
| 5,141,850 A | 8/1992 | Cole et al. |
| 5,143,080 A | 9/1992 | York |
| 5,202,261 A | 4/1993 | Musho et al. |
| 5,211,055 A | 5/1993 | Steudle et al. |
| 5,218,088 A | 6/1993 | Gorenstein et al. |
| 5,221,457 A | 6/1993 | North et al. |
| 5,230,864 A | 7/1993 | Columbus |
| 5,353,802 A | 10/1994 | Ollmar |
| 5,388,449 A | 2/1995 | Leveen et al. |
| 5,461,699 A | 10/1995 | Arbabi et al. |
| 5,489,515 A | 2/1996 | Hatschek et al. |
| 5,522,805 A | 6/1996 | Vancaillie et al. |
| 5,571,568 A | 11/1996 | Ribi et al. |
| 5,591,636 A | 1/1997 | Grass |
| 5,591,645 A | 1/1997 | Rosenstein |
| 5,602,040 A | 2/1997 | May et al. |
| 5,605,662 A | 2/1997 | Heller et al. |
| 5,620,584 A | 4/1997 | Reetz et al. |
| 5,656,503 A | 8/1997 | May et al. |
| 5,665,904 A | 9/1997 | Boeling |
| 5,714,389 A | 2/1998 | Charlton et al. |
| 5,739,376 A | 4/1998 | Bingel |
| 5,766,435 A | 6/1998 | Liao et al. |
| 5,772,585 A | 6/1998 | Lavin et al. |
| 5,798,031 A | 8/1998 | Charlton et al. |
| 5,810,725 A | 9/1998 | Sugihara et al. |
| 5,821,399 A | 10/1998 | Zelin |
| 5,849,208 A | 12/1998 | Hayes et al. |
| 5,849,486 A | 12/1998 | Heller et al. |
| 5,851,489 A | 12/1998 | Wolf et al. |
| 5,869,231 A | 2/1999 | Roemisch et al. |
| 5,959,671 A | 9/1999 | Etoh et al. |
| 5,965,631 A | 10/1999 | Nicolson et al. |
| 5,989,921 A | 11/1999 | Charlton et al. |
| 5,994,410 A | 11/1999 | Chiang et al. |
| 5,997,817 A | 12/1999 | Crismore et al. |
| 6,038,554 A | 3/2000 | Vig |
| 6,048,690 A | 4/2000 | Heller et al. |
| 6,090,251 A | 7/2000 | Sundberg et al. |
| 6,117,643 A | 9/2000 | Simpson et al. |
| 6,120,460 A | 9/2000 | Abreu |
| 6,120,676 A | 9/2000 | Heller et al. |
| 6,144,869 A | 11/2000 | Berner et al. |
| 6,162,926 A | 12/2000 | Murphy et al. |
| 6,183,714 B1 | 2/2001 | Smalley et al. |
| 6,214,208 B1 | 4/2001 | Ando et al. |
| 6,224,550 B1 | 5/2001 | Ellingsen |
| 6,319,676 B1 | 11/2001 | Nazareth et al. |
| 6,341,232 B1 | 1/2002 | Conn et al. |
| 6,344,272 B1 | 2/2002 | Oldenburg et al. |
| 6,356,776 B1 | 3/2002 | Berner et al. |
| 6,403,317 B1 | 6/2002 | Anderson |
| 6,423,001 B1 | 7/2002 | Abreu |
| 6,485,982 B1 | 11/2002 | Charlton |
| 6,529,277 B1 | 3/2003 | Weitekamp |
| 6,544,193 B2 | 4/2003 | Abreu |
| 6,558,945 B1 | 5/2003 | Kao |
| 6,583,220 B1 | 6/2003 | Lipman |
| 6,594,514 B2 | 7/2003 | Berner et al. |
| 6,602,400 B1 | 8/2003 | Choong et al. |
| 6,602,469 B1 | 8/2003 | Maus et al. |
| 6,630,307 B2 | 10/2003 | Bruchez et al. |
| 6,633,772 B2 | 10/2003 | Ford et al. |
| 6,682,895 B2 | 1/2004 | Mirkin et al. |
| 6,695,964 B1 | 2/2004 | Ando et al. |
| 6,740,518 B1 | 5/2004 | Duong et al. |

(56) References Cited

U.S. PATENT DOCUMENTS

| | | |
|---|---|---|
| 6,750,016 B2 | 6/2004 | Mirkin et al. |
| 6,767,702 B2 | 7/2004 | Mirkin et al. |
| 6,773,884 B2 | 8/2004 | Mirkin et al. |
| 6,777,186 B2 | 8/2004 | Mirkin et al. |
| 6,778,316 B2 | 8/2004 | Halas et al. |
| 6,850,790 B2 | 2/2005 | Berner et al. |
| 6,884,356 B2 | 4/2005 | Kosenka et al. |
| 6,894,511 B2 | 5/2005 | Yukimasa et al. |
| 6,955,881 B2 | 10/2005 | Tanaami |
| 7,017,394 B2 | 3/2006 | Sullivan |
| 7,021,122 B1 | 4/2006 | Rosemberg et al. |
| 7,051,569 B2 | 5/2006 | Sullivan et al. |
| 7,111,502 B2 | 9/2006 | Sullivan et al. |
| 7,127,957 B2 | 10/2006 | Mathur et al. |
| 7,129,717 B2 | 10/2006 | Donsky |
| 7,133,712 B2 | 11/2006 | Cohan et al. |
| 7,174,199 B2 | 2/2007 | Berner et al. |
| 7,204,122 B2 | 4/2007 | Sullivan et al. |
| 7,258,769 B2 | 8/2007 | Cui et al. |
| 7,344,679 B2 | 3/2008 | Natarajan et al. |
| 7,395,103 B2 | 7/2008 | Cappo et al. |
| 7,449,307 B2 | 11/2008 | Cima et al. |
| 7,574,902 B2 | 8/2009 | Sullivan |
| 7,763,454 B2 | 7/2010 | Nazareth et al. |
| 7,810,380 B2 | 10/2010 | Donsky et al. |
| 7,873,399 B2 | 1/2011 | Berner et al. |
| 7,905,134 B2 | 3/2011 | Sullivan |
| 7,914,460 B2 | 3/2011 | Melker et al. |
| 7,964,390 B2 | 6/2011 | Rozakis et al. |
| 7,987,702 B2 | 8/2011 | Sullivan |
| 8,020,433 B2 | 9/2011 | Sullivan et al. |
| 8,249,682 B2 | 8/2012 | Cappo et al. |
| 8,309,362 B2 | 11/2012 | Palleschi et al. |
| 8,551,422 B2 | 10/2013 | Wan et al. |
| 8,627,712 B2 | 1/2014 | Donsky et al. |
| 8,628,731 B2 | 1/2014 | Donsky et al. |
| 8,713,997 B2 | 5/2014 | Donsky et al. |
| 9,217,701 B2 | 12/2015 | Sullivan |
| 9,217,702 B2 | 12/2015 | Sullivan |
| 9,335,243 B2 | 5/2016 | Donsky et al. |
| 2002/0031813 A1 | 3/2002 | Ozkan et al. |
| 2002/0041829 A1 | 4/2002 | Kowallis |
| 2002/0042065 A1 | 4/2002 | Han et al. |
| 2002/0094580 A1 | 7/2002 | Jorgenson et al. |
| 2002/0098526 A1* | 7/2002 | Bamdad ............ C12Q 1/6816 |
| | | 435/6.16 |
| 2002/0127574 A1 | 9/2002 | Mirkin et al. |
| 2002/0182627 A1 | 12/2002 | Wang et al. |
| 2002/0196429 A1 | 12/2002 | Russell et al. |
| 2003/0003458 A1 | 1/2003 | Pinkel et al. |
| 2003/0013109 A1 | 1/2003 | Ballinger et al. |
| 2003/0054342 A1 | 3/2003 | Star et al. |
| 2003/0080087 A1 | 5/2003 | Stelzle |
| 2003/0143580 A1 | 7/2003 | Straus |
| 2004/0023415 A1 | 2/2004 | Sokolov et al. |
| 2004/0076547 A1 | 4/2004 | Carney et al. |
| 2004/0086897 A1 | 5/2004 | Mirkin et al. |
| 2004/0099813 A1 | 5/2004 | Eggeling et al. |
| 2004/0110220 A1 | 6/2004 | Mirkin et al. |
| 2004/0146918 A1 | 7/2004 | Weiner et al. |
| 2004/0147031 A1 | 7/2004 | Nakao |
| 2004/0186359 A1 | 9/2004 | Beaudoin et al. |
| 2004/0220089 A1 | 11/2004 | Ellis et al. |
| 2005/0032204 A1 | 2/2005 | Rodgers et al. |
| 2005/0106714 A1 | 5/2005 | Zarur et al. |
| 2005/0148043 A1 | 7/2005 | Dale |
| 2005/0176029 A1 | 8/2005 | Heller et al. |
| 2005/0201895 A1 | 9/2005 | Donsky |
| 2005/0224345 A1 | 10/2005 | Taniike et al. |
| 2005/0239116 A1 | 10/2005 | Willey |
| 2005/0255453 A1 | 11/2005 | Qian et al. |
| 2005/0277202 A1* | 12/2005 | Fleming ............ G01N 33/558 |
| | | 436/514 |
| 2006/0127964 A1 | 6/2006 | Ford et al. |
| 2006/0141469 A1 | 6/2006 | Rossier et al. |
| 2006/0292039 A1 | 12/2006 | Iida |
| 2007/0031283 A1 | 2/2007 | Davis et al. |
| 2007/0043283 A1 | 2/2007 | Cohan et al. |
| 2007/0269906 A1* | 11/2007 | Wang .................. G01N 33/536 |
| | | 436/536 |
| 2008/0038839 A1 | 2/2008 | Linder et al. |
| 2008/0050282 A1 | 2/2008 | Natarajan et al. |
| 2008/0053206 A1 | 3/2008 | Natarajan et al. |
| 2008/0057569 A1 | 3/2008 | Natarajan et al. |
| 2008/0103376 A1 | 5/2008 | Felder |
| 2008/0148821 A1 | 6/2008 | Donsky et al. |
| 2008/0154179 A1 | 6/2008 | Cantor et al. |
| 2008/0264151 A1 | 10/2008 | Sullivan et al. |
| 2008/0264152 A1 | 10/2008 | Sullivan |
| 2008/0273171 A1 | 11/2008 | Huth et al. |
| 2008/0286750 A1 | 11/2008 | Xu et al. |
| 2009/0221431 A1 | 9/2009 | Yoo |
| 2009/0241647 A1 | 10/2009 | Sullivan |
| 2010/0216175 A1 | 8/2010 | Melker et al. |
| 2011/0054938 A1 | 3/2011 | Hood et al. |
| 2012/0067112 A1 | 3/2012 | Sullivan et al. |
| 2012/0184046 A1 | 7/2012 | Atkin |
| 2012/0270225 A1* | 10/2012 | Wakeley ............ C12Q 1/6834 |
| | | 435/6.12 |
| 2013/0001102 A1 | 1/2013 | Palleschi et al. |
| 2013/0008803 A1 | 1/2013 | Meyerhoff et al. |
| 2013/0175185 A1 | 7/2013 | Donsky et al. |
| 2013/0220833 A1 | 8/2013 | Sullivan |
| 2013/0233061 A1 | 9/2013 | Sullivan |
| 2014/0088381 A1 | 3/2014 | Etzkorn et al. |
| 2014/0124382 A1 | 5/2014 | Edelbrock et al. |
| 2015/0017068 A1 | 1/2015 | Sturman et al. |
| 2015/0045694 A1 | 2/2015 | Sullivan et al. |
| 2015/0064800 A1* | 3/2015 | Chance ............ G01N 33/6863 |
| | | 436/501 |
| 2015/0226752 A1* | 8/2015 | Nazareth .......... G01N 33/54366 |
| | | 436/501 |
| 2016/0282252 A1 | 9/2016 | Sullivan |
| 2017/0108423 A1 | 4/2017 | Donsky et al. |

FOREIGN PATENT DOCUMENTS

| | | |
|---|---|---|
| DE | 10050883 A1 | 5/2002 |
| EP | 0391674 A2 | 10/1990 |
| EP | 0467219 A1 | 1/1992 |
| EP | 0571066 A2 | 11/1993 |
| GB | 2102963 A | 2/1983 |
| JP | S535690 U | 1/1978 |
| JP | S5542048 A | 3/1980 |
| JP | S6396455 A | 4/1988 |
| JP | S63148159 A | 6/1988 |
| JP | H0353550 A | 3/1991 |
| JP | H0363550 A | 3/1991 |
| JP | H03505785 A | 12/1991 |
| JP | H0622793 A | 2/1994 |
| JP | H06296595 A | 10/1994 |
| JP | H07191023 A | 7/1995 |
| JP | H07506431 A | 7/1995 |
| JP | H07218510 A | 8/1995 |
| JP | H07239313 A | 9/1995 |
| JP | H0961312 A | 3/1997 |
| JP | 2619305 B2 | 6/1997 |
| JP | 2000508528 A | 7/2000 |
| JP | 2000509507 A | 7/2000 |
| JP | 2002176999 A | 6/2002 |
| JP | 2003520958 A | 7/2003 |
| JP | 2003527580 A | 9/2003 |
| JP | 2004528537 A | 9/2004 |
| JP | 2006112881 A | 4/2006 |
| JP | 2007268486 A | 10/2007 |
| JP | 2009511886 A | 3/2009 |
| JP | 2010122237 A | 6/2010 |
| JP | 2010203779 A | 9/2010 |
| JP | 2012255802 A | 12/2012 |
| JP | 2013170835 A | 9/2013 |
| WO | WO-8700286 A1 | 1/1987 |
| WO | WO-9007902 A1 | 7/1990 |
| WO | WO-9012314 A1 | 10/1990 |

(56) References Cited

FOREIGN PATENT DOCUMENTS

| WO | WO-9322054 A1 | 11/1993 |
|---|---|---|
| WO | WO-9322058 A1 | 11/1993 |
| WO | WO-9614571 A1 | 5/1996 |
| WO | WO-9736681 A1 | 10/1997 |
| WO | WO-9835225 A1 | 8/1998 |
| WO | WO-9838334 A1 | 9/1998 |
| WO | WO-9923938 A1 | 5/1999 |
| WO | WO-9931503 A1 | 6/1999 |
| WO | WO-9947907 A1 | 9/1999 |
| WO | WO-0035365 A1 | 6/2000 |
| WO | WO-0062047 A1 | 10/2000 |
| WO | WO-0125769 A2 | 4/2001 |
| WO | WO-0134764 A2 | 5/2001 |
| WO | WO-0143875 A1 | 6/2001 |
| WO | WO-0153798 A1 | 7/2001 |
| WO | WO-0183674 A1 | 11/2001 |
| WO | WO-02054067 A2 | 7/2002 |
| WO | WO-02059598 A1 | 8/2002 |
| WO | WO-02103354 A1 | 12/2002 |
| WO | WO-03068963 A1 | 8/2003 |
| WO | WO-2004017050 A1 | 2/2004 |
| WO | WO-2005040755 A2 | 5/2005 |
| WO | WO-2005051309 A2 | 6/2005 |
| WO | WO-2005076796 A2 | 8/2005 |
| WO | WO-2005089207 A2 | 9/2005 |
| WO | WO-2005089210 A2 | 9/2005 |
| WO | WO-2005094286 A2 | 10/2005 |
| WO | WO-2005076796 A3 | 5/2006 |
| WO | WO-2008044530 A1 | 4/2008 |
| WO | WO-2008073399 A1 | 6/2008 |
| WO | WO-2008119069 A1 | 10/2008 |
| WO | WO-2008128248 A1 | 10/2008 |
| WO | WO-2011099569 A1 | 8/2011 |
| WO | WO-2016049221 A1 | 3/2016 |

OTHER PUBLICATIONS

U.S. Appl. No. 14/332,241 Office Action dated Feb. 9, 2018.
Zimmermann et al. Valves for autonomous capillary systems. Microfluid Nanfluid 5(3):395-402 (2008).
Bhanot et al. The Importance of Thermodynamic Equilibrium for High Throughput Gene Expression Arrays. Biophysical J. 84:124-135 (2003).
Borisenko et al. Simultaneous Optical and Electrical Recording of Single Gramicidin Channels. Biophysical J. 84(1):612-622 (2003).
Braun et al. Lock-in by molecular multiplication. Applied Physics Ltrs 83(26):5554-5556 (2003).
Certified English Translation for German Patent No. DE 3414866 entitled: Method and device to measure the osmolarity of liquid samples.
Chandler et al. Detection of Calcium Signals in Neutrophils Using Fluorescent Dyes. Luminescence Applications 383:70-83 (1989).
Claudino et al. BIOSIS Abstract #002246922. The role of cGMP on uroguanylin responses in salt-loaded rats. Annual Meeting of Professional Research Scientists on Experimental Biology, New Orleans, Louisiana, USA Apr. 20-24, 2002, FASEB Journal 16:A956 (Mar. 22, 2002).
Farris. Tear Osmolarity—A New Gold Standard, pp. 495-503 (1994).
Fritzche et al. Metal nanoparticles as labels for heterogeneous, chip-based DNA detection. Nanotechnology 14(12):R63-R73 (2003).
Geerling et al. Quality of salivary tears following autologous submandibular gland transplantation for severe dry eye. Graefes Arch Clin Exp Opthalmol 238:45-52 (2000).
Gilbard et al. Changes in tear ion concentration dry-eye disorders. Lacrimal Gland, Tear Film, and Dry Eye Syndromes, pp. 529-533 (May 2001).
Grodzinsky. Fields, forces and flows in biological tissues and membranes. MIT Dept. of Engineering. pp. 191-197 (1995).
Kung et al. Adaptive Principal Component Extraction (APEX) and Applications. IEEE Transactions on signal Processing 42(5):1202-1217 (1994).
Lemp. Report of the National Eye Institute/Industry Workshop on Clinical Trials in Dry Eyes. The CLAO Journal 21(4):221-232 (1995).
Mitsubaiyashi et al. Flexible Conductimetric Sensor. Anal. Chem. 65:3586-3590 (1993).
Nishihara et al. Method for Measuring Concentration of Drug in Tear Fluid, Examination and Technique. 18(6):892-893 (1990).
Ogasawara et al. Conductance and turnover rate of tear fluid in healthy and keratoconjunctivitis sicca subjects. Japanese Journal of Clinical Ophthalmology 49:779-783 (1995) (English Abstract).
Ogasawara et al. Electrical conductivity of tear fluid in healthy persons and keratoconjunctivitis sicca patients measured by a flexible conductimetric sensor. Graefes Arch Clin Exp Ophthalmol 234:542-546 (1996).
Ogasawara et al. Tear Electrolyte Concentration and Tear Turnover Rate in Normal Healthy Persons as Determined by Flexible Conductimetric Sensor. Journal of the Eye 11(9):1385-1388 (1994) (English Abstract).
Papageorgiou et al. A sensitive method for the estimation of the cytoplasmic osmolality of cyanobacterial cells using chlorophyll a fluorescence. Biochim Biophys Acta 1335:1-4 (1997).
PCT/US2003/09553 International Preliminary Examination Report dated Nov. 18, 2004.
PCT/US2003/09553 International Search Report dated Oct. 10, 2003.
PCT/US2004/034844 International Preliminary Report on Patentability dated Apr. 24, 2006.
PCT/US2004/034844 International Search Report dated Oct. 21, 2005.
PCT/US2004/039128 International Preliminary Report on Patentability dated Mar. 3, 2009.
PCT/US2004/039128 International Search Report dated May 21, 2008.
PCT/US2005/001573 International Search Preliminary Report on Patentability dated Aug. 7, 2006.
PCT/US2005/001573 International Search Report and Written Opinion dated Mar. 6, 2006.
PCT/US2005/008107 International Search Report dated Jan. 13, 2006.
PCT/US2005/10230 International Preliminary Report on Patentability dated Sep. 26, 2006.
PCT/US2005/10230 International Search Report dated Feb. 14, 2006.
PCT/US2007/25277 International Preliminary Report on Patentability dated Jun. 16, 2009.
PCT/US2007/25277 International Search Report dated May 13, 2008.
PCT/US2008/058731 International Preliminary Report on Patentability dated Sep. 29, 2009.
PCT/US2008/058731 International Search Report dated Jul. 11, 2008.
PCT/US2008/060526 International Preliminary Report on Patentability dated Oct. 20, 2009.
PCT/US2008/060526 International Search Report dated Jul. 10, 2008.
PCT/US2015/051772 International Preliminary Report on Patentability dated Apr. 6, 2017.
PCT/US2015/051772 International Search Report and Written Opinion dated Dec. 16, 2015.
Pensyl et al. Vapor Pressure Osmometry: Minimum Sample Microvolumes. Acta Ophthalmol Scan 77(1):27-30 (1999).
Schaumberg. Aging and sex-steroid hormone influences in dry eye syndrome. ARVO Abstract from IOVS 42(4):S2 (Mar. 15, 2001).
U.S. Appl. No. 10/400,617 Office Action dated Feb. 23, 2005.
U.S. Appl. No. 10/400,617 Office Action dated Jul. 15, 2005.
U.S. Appl. No. 10/718,498 Office Action dated Apr. 14, 2006.
U.S. Appl. No. 10/718,498 Office Action dated Sep. 28, 2005.
U.S. Appl. No. 10/772,084 Office Action dated Sep. 28, 2005.
U.S. Appl. No. 10/810,780 Office Action dated Dec. 9, 2005.
U.S. Appl. No. 11/358,986 Office Action dated Jul. 25, 2006.
U.S. Appl. No. 11/358,986 Office Action dated Sep. 11, 2008.
U.S. Appl. No. 12/001,243 Office Action dated Mar. 29, 2010.
U.S. Appl. No. 12/058,428 Office Action dated Aug. 19, 2010.

(56) References Cited

OTHER PUBLICATIONS

U.S. Appl. No. 12/435,193 Office Action dated Nov. 24, 2010.
U.S. Appl. No. 12/874,088 Office Action dated Jan. 22, 2013.
U.S. Appl. No. 13/031,051 Office Action dated Feb. 26, 2015.
U.S. Appl. No. 13/204,542 Office Action dated Mar. 20, 2014.
U.S. Appl. No. 13/299,197 Office Action dated Apr. 2, 2015.
U.S. Appl. No. 13/299,277 Office Action dated Aug. 6, 2013.
U.S. Appl. No. 13/299,277 Office Action dated Jan. 23, 2013.
U.S. Appl. No. 13/779,597 Office Action dated Apr. 25, 2014.
U.S. Appl. No. 13/779,597 Office Action dated Aug. 28, 2013.
U.S. Appl. No. 13/779,597 Office Action dated Feb. 25, 2016.
U.S. Appl. No. 13/779,597 Office Action dated Jan. 15, 2015.
U.S. Appl. No. 13/779,597 Office Action dated Jul. 31, 2015.
U.S. Appl. No. 13/779,597 Office Action dated Sep. 9, 2016.
U.S. Appl. No. 13/802,534 Office Action dated Jul. 26, 2013.
U.S. Appl. No. 13/842,409 Office Action dated Jan. 15, 2015.
U.S. Appl. No. 13/842,409 Office Action dated Sep. 18, 2015.
U.S. Appl. No. 13/842,474 Office Action dated Dec. 10, 2015.
U.S. Appl. No. 13/842,474 Office Action dated Jul. 9, 2015.
U.S. Appl. No. 14/332,241 Office Action dated Dec. 2, 2016.
U.S. Appl. No. 14/332,241 Office Action dated May 15, 2017.
Vollmer et al. Multiplexed DNA Quantification by Spectroscopic Shift of Two Microsphere Cavities. Biophysical Journal 85:1974-1979 (2003).
U.S. Appl. No. 15/175,698 Office Action dated Apr. 18, 2018.
U.S. Appl. No. 15/362,283 Office Action dated Sep. 20, 2018.

\* cited by examiner

SYSTEMS AND METHODS FOR INTEGRATION OF MICROFLUIDIC TEAR COLLECTION AND LATERAL FLOW ANALYSIS OF ANALYTES OF INTEREST

CROSS-REFERENCE TO RELATED APPLICATIONS

This application is the National Phase Entry of International Application No. PCT/US2015/051772, filed on Sep. 23, 2015, which claims the benefit of and priority under 35 U.S.C. 119(e) to U.S. Provisional patent application Ser. No. 62/053,923, entitled "Systems and Methods for Integration of Microfluidic Tear Collection and Lateral Flow Analysis of Analytes of Interest" filed Sep. 23, 2014, the entire disclosure of each is incorporated herein by reference.

BACKGROUND

Tears fulfill an essential role in maintaining ocular surface integrity, protecting against microbial challenge, and preserving visual acuity. These functions, in turn, are critically dependent upon the composition and stability of the tear film structure, which includes an underlying mucin foundation, a middle aqueous component, and an overlying lipid layer. Disruption, deficiency, or absence of the tear film can severely impact the eye. If unmanaged with artificial tear substitutes or tear film conservation therapy, these disorders can lead to intractable desiccation of the corneal epithelium, ulceration and perforation of the cornea, an increased incidence of infectious disease, and ultimately pronounced visual impairment and blindness.

Keratoconjunctivitis sicca (KCS), or "dry eye", is a condition in which one or more of the tear film structure components listed above is present in insufficient volume or is otherwise out of balance with the other components. Fluid tonicity or osmolarity of tears increases in patients with KCS. KCS is associated with conditions that affect the general health of the body, such as Sjogren's syndrome, aging, and androgen deficiency.

SUMMARY

Osmolarity of a tear film is a sensitive and specific indicator for the diagnosis of KCS and other conditions. The osmolarity of a sample fluid (as a non-limiting example, a tear) is determined, as a non-limiting example, by an ex vivo technique called "freezing point depression," in which solutes or ions in a solvent (as a non-limiting example, water), cause a lowering of the fluid freezing point from what it would be without the ions. In the freezing point depression analysis the freezing point of the ionized sample fluid is found by detecting the temperature at which a quantity of the sample (typically on the order of about several milliliters) first begins to freeze in a container (as a non-limiting example, a tube). To measure the freezing point, a volume of the sample fluid is collected into a container, such as a tube. Next, a temperature probe is immersed in the sample fluid, and the container is brought into contact with a freezing bath or Peltier cooling device. The sample is continuously stirred so as to achieve a supercooled liquid state below its freezing point. Upon mechanical induction, the sample solidifies, rising to its freezing point due to the thermodynamic heat of fusion. The deviation from the sample freezing point from 0° C. is proportional to the solute level in the sample fluid. This type of measuring device is sometimes referred to as an osmometer.

Presently, freezing point depression measurements are made ex vivo by removing tear samples from the eye using a micropipette or capillary tube and measuring the depression of the freezing point that results from heightened osmolarity. However, these ex vivo measurements are often plagued by many difficulties. For example, to perform freezing point depression analysis of the tear sample, a relatively large volume must be collected, typically on the order of 20 microliters (µL) of a tear film. Because no more than about 10 to about 100 nanoliters (nL) of tear sample is obtained at any one time from a KCS patient, the collection of sufficient amounts of fluid for conventional ex vivo techniques requires a physician to induce reflex tearing in the patient. Reflex tearing is caused by a sharp or prolonged irritation to the ocular surface, akin to when a large piece of dirt becomes lodged in one's eye. Reflex tears are more dilute, in other words, they have fewer solute ions than the tears that are normally found on the eye. Any dilution of the tear film invalidates the diagnostic ability of an osmolarity test for dry eye, and therefore make currently available ex vivo methods prohibitive in a clinical setting.

A similar ex vivo technique is vapor pressure osmometry, where a small, circular piece of filter paper is lodged underneath a patient's eyelid until sufficient fluid is absorbed. The filter paper disc is placed into a sealed chamber, whereupon a cooled temperature sensor measures the condensation of vapor on its surface. Eventually the temperature sensor is raised to the dew point of the sample. The reduction in dew point proportional to water is then converted into osmolarity. Because of the induction of reflex tearing and the large volume requirements for existing vapor pressure osmometers, these techniques are currently impractical for determination of dry eye.

The Clifton Nanoliter Osmometer (available from Clifton Technical Physics of Hartford, N.Y., USA) has been used extensively in laboratory settings to quantify the solute concentrations of KCS patients, but the machine requires a significant amount of training to operate. The operation of this instrument generally requires hour-long calibrations and a skilled technician in order to generate acceptable data. The Clifton Nanoliter Osmometer is also bulky and relatively expensive. These characteristics seriously detract from it use as a clinical osmometer.

In addition, blink-to-blink changes in the osmolarity of the tear film is a fundamental characteristic of dry eye disease. These blink-to-blink changes, driven by evaporation and water loss from an unstable tear film, increase in amplitude with increasing disease severity, leading to a chaotic concentration profile of analytes of interest between blinks. Simultaneous or serial measurement of tear osmolarity and analytes of interest is useful, since one may compensate for the biological variation of dry eye disease by normalizing against the sample osmotic pressure.

Existing techniques for measuring analytes within the tear film require collection of large volumes of tear film, using either repeated dabbing of the ocular surface with a sponge, placing filter paper similar to a Schirmer strip under the eyelid of a patient, or by conjunctival impression cytology where paper is pressed up against the conjunctiva to subsequently peel off a surface layer of cells. In research settings, microliters of tear are collected using repeated sampling into a capillary tube, but this technique requires special training and, in some instances, requires ten minutes or longer on a dry eye patient to obtain the volumes required to run existing assays. These techniques all introduce the risk of reflex tearing, which produces a hypoosmolar fluid biased towards lacrimal output rather than the basal tear that is more reflective of the contributions from the entire ocular surface and meibomian gland.

It should be apparent from the discussion above that integrated collection and measurement techniques for analytes of interest and tear osmolarity are generally unavailable in a clinical setting and are unable to attain the small volumes available from most patients. Thus, there is a need for an improved, clinically feasible, nanoliter-scale osmolarity and analyte measurement techniques. The present invention satisfies this need with devices having a variety of improvements for small volume analysis.

The present disclosure provides systems, methods, and devices for analyzing fluidic samples, such as tear samples.

The approaches described herein permit the detection of one or more properties of a fluidic sample of interest (as non-limiting examples, osmolarity, analyte concentration, or both) using a single microfluidic device, thereby producing one or more sample readings that, in some embodiments, are quantified and used to diagnose various medical conditions. In certain embodiments, the invention permits a plurality of different analyses to be performed on a single sample volume, thereby increasing the speed, versatility, and convenience of diagnostic testing. Furthermore, the systems, methods, and devices of the present disclosure are suitable for use with small sample volumes (as non-limiting examples, microliter or nanoliter volumes), which is particularly beneficial for applications in which only limited amounts of sample are available, as a non-limiting example, tear film samples for analysis of eye conditions.

In some embodiments, there are provided devices for analyzing a fluidic sample comprising: a first sample region shaped to receive a volume of the fluidic sample and comprising at least one transducer configured to detect an energy property of the volume in order to generate a first sample reading; and a second sample region in fluidic communication with the first sample-receiving portion and shaped to receive at least a portion of the volume, wherein the second sample region comprises a detection substrate configured to detect one or more analyte in the at least a portion of the volume in order to generate a second sample reading.

In some embodiments, the devices further comprise a metering mechanism that controls flow of the volume from the first sample region into the second sample region. In some embodiments, the metering mechanism comprises a passive valve or an active valve. Non-limiting exemplary passive valves include one or more geometric features that constrain fluid flow to the second sample region. In some embodiments, the passive valve is comprised of a discontinuity in the hydrophilicity of the receiving substrate. In some embodiments, a passive valve is overcome by a pressurized fluidic volume. In some embodiments, a passive valve as disclosed herein is actuated at least by mechanical energy of a fluid. In some embodiments, the fluid is one or more liquid, one or more gases, or combinations thereof. In some embodiments, the fluid is the sample fluid, a wash fluid, or a transfer fluid. In some embodiments, a passive valve as disclosed herein does not require any energy source external to the elements of the system as disclosed herein for its proper functioning. In some embodiments, a passive valve requires no extra energy other than the energy of fluid and/or energy of capillary action, or energy transformed therefrom. Alternatively or in combination, the metering mechanism comprises an active valve, in some embodiments. In some embodiments, the active valve comprises an electrode having a hydrophobic coating (as a non-limiting example, an alkanethiol self-assembled monolayer (SAM)). In some embodiments, a voltage is applied to the electrode in order to cause dissolution of the hydrophobic coating, thereby permitting flow of the volume into the second sample region. In some embodiments, an active valve as disclosed herein requires an electrical energy source from elements internal or external to the device or system as disclosed herein for its proper functioning. In some embodiments, an active valve requires extra energy in addition to the energy of fluid and/or energy of the capillary action, or energy transformed therefrom. In some embodiments, the valve as disclosed herein is unidirectional. In other embodiments, the valve is configured to allow passage of fluidic volume in both directions. In some embodiments, the passive valve or the active valve includes one or more selected from: a balanced valve, a tip valve, and a vent valve.

In some embodiments, the first sample region comprises a capillary channel. In some embodiments, the at least one transducer is situated on a wall of the capillary channel. In some embodiments, the least one wall of the capillary channel comprises a layer of pressure-sensitive adhesive. In some embodiments, the layer of pressure-sensitive adhesive interacts with the volume so as to delay flow of the volume through the capillary channel.

In some embodiments, the fluidic sample comprises tear fluid.

In some embodiments, the first sample reading is indicative of osmolarity of the fluidic sample. In some embodiments, the second sample reading is indicative of concentration of the one or more analytes in the fluidic sample. In some embodiments, the first sample reading is indicative of osmolarity of the fluidic sample, and the second sample reading is indicative of concentration of the one or more analytes in the fluidic sample.

In some embodiments, the volume is within a range from about 10 nL to about 10 µL, such as within a range from about 50 nL to about 250 nL. In some embodiments, the volume is within a range between any two of the following: about 10 nL, about 20 nL, about 30 nL, about 40 nL, about 50 nL, about 60 nL, about 70 nL, about 80 nL, about 90 nL, about 100 nL, about 150 nL, about 200 nL, about 250 nL, about 300 nL, about 400 nL, about 500 nL, about 600 nL, about 700 nL, about 800 nL, about 900 nL, about 1 µL, about 2 µL, about 3 µL, about 4 µL, about 5 µL, about 6 µL, about 7 µL, about 8 µL, about 9 µL, or about 10 µL. In some embodiments, the volume is no more than about 20 µL, about 250 nL, about 200 nL, or about 50 nL. In some embodiments, the volume is no more than about 10 nL, about 20 nL, about 30 nL, about 40 nL, about 50 nL, about 60 nL, about 70 nL, about 80 nL, about 90 nL, about 100 nL, about 150 nL, about 200 nL, about 250 nL, about 300 nL, about 400 nL, about 500 nL, about 600 nL, about 700 nL, about 800 nL, about 900 nL, about 1 µL, about 2 µL, about 3 µL, about 4 µL, about 5 µL, about 6 µL, about 7 µL, about 8 µL, about 9 µL, or about 10 µL.

In some embodiments, the devices further comprise a reservoir of transfer fluid in fluidic communication with the first sample region. In some embodiments, the introduction of the transfer fluid from the reservoir into the first sample region causes at least a portion of the volume to be displaced from the first sample region into the second sample region. In some embodiments, a controlled flow is used to match the capillary wicking rate of the microporous substrate with the fluidic pumping rate from the reservoir. In other embodiments, an air pulse displaces the fluid in the first sample region into the second sample region.

In some embodiments, the sample fluid is allowed to incubate with a reagent (as non-limiting examples, an antibody or an antigen binding fragment thereof, or a biosynthetic antibody binding site, such as an scFv, aptamer, avibody, peptide, PNA, functionalized nanoparticle, etc.) within the first sample region, to facilitate detection of an analyte in the second sample region. In some embodiments, the reagent is contained within the microporous substrate or other intermediate layer such as a glass conjugate pad, whereupon the breach of the passive valve introduces the sample fluid to an incubation region on the microporous substrate. In other embodiments, the sample fluid is first flowed through the transduction area of the first or second sample region, followed by rehydration and transport of an upstream detection moiety using fluid from the reservoir.

In some embodiments, the detection substrate includes a microporous substrate and a fluidic volume flows through the microporous substrate. In some embodiments, the detection substrate comprises a microporous substrate and, during operation, the at least a portion of the volume traverses the microporous substrate. In some embodiments, the microporous substrate has a geometry configured to facilitate a substantially uniform fluid front as at least a portion of the volume traverses the microporous substrate in the direction of flow. In some embodiments, the fluidic volume includes one or more liquids, one or more gases, or combinations thereof. In further embodiments, the fluidic volume includes at least the sample fluid. In some embodiments, the fluidic volume is greater than or equal to a minimal volume in order to generate at least one valid sample reading. In some embodiments, the fluidic volume is greater than or equal to a minimal volume in order to generate at least one valid sample reading from the first sample region and at least one valid sample reading from the second sample region. In some embodiments, the microporous substrate has a geometry shaped to generate or increase flow homogenization of the volume as it flows through the microporous substrate. In some embodiments, the microporous substrate has an hourglass-shaped geometry. In some embodiments, the microporous substrate has a center serpentine channel surrounded by more linear, shorter path-length rehydration channels. In some embodiments, the microporous substrate comprises a plurality of openings for increasing flow homogenization. In other embodiments, the microporous substrate is shaped to effect preferential rehydration of high resistance areas. In yet other embodiments, the microporous substrate is shaped to allow a rehydration flow to move through low resistance or low path length areas while the sample fluid is delayed through higher resistance or higher path length areas.

Disclosed herein, in some embodiments, are methods for analyzing a fluidic sample comprising: introducing a volume of the fluidic sample into a first sample region; detecting an energy property of the volume within the first sample region using at least one transducer, thereby generating a first sample reading; flowing at least a portion of the volume into a second sample region; and detecting one or more analytes in at least a portion of the volume within the second sample region using a detection substrate, thereby generating a second sample reading.

In some embodiments, the methods further comprise controlling fluid flow from the first sample region to the second sample region using a metering mechanism. In some embodiments, the metering mechanism comprises a passive valve. In some embodiments, the metering mechanism comprises one or more geometric features that constrain fluid flow to the second sample region. In other embodiments, the method further arrests fluid flow using a discontinuity in the hydrophilicity of the receiving substrate. Alternatively or in combination, in some embodiments, the metering mechanism comprises an active valve. In some embodiments, the active valve comprises an electrode having a hydrophobic coating (as a non-limiting example, an alkanethiol self-assembled monolayer (SAM)). In some embodiments, a voltage is applied to the electrode in order to cause dissolution of the hydrophobic coating, thereby permitting fluid flow to the second sample region. In some embodiments, a pressurized wash fluid is used to overcome a passive valve and transport the sample fluid to the second sample region. In some embodiments, the first sample region comprises a capillary channel. In some embodiments, the at least one transducer is situated on a wall of the capillary channel. In some embodiments, the at least one wall of the capillary channel comprises a layer of pressure-sensitive adhesive. In some embodiments, the layer of pressure-sensitive adhesive interacts with the volume so as to delay flow of the volume through the capillary channel.

In some embodiments, the fluidic sample comprises tear fluid.

In some embodiments, the first sample reading is indicative of osmolarity of the fluidic sample. In some embodiments, the second sample reading is indicative of concentration of the one or more analytes in the fluidic sample. In some embodiments, the first sample reading is indicative of osmolarity of the fluidic sample, and the second sample reading is indicative of concentration of the one or more analytes in the fluidic sample.

In some embodiments, the volume is within a range from about 10 nL to about 10 µL, such as within a range from about 50 nL to about 250 nL. In some embodiments, the volume is within a range between any two of the following: about 10 nL, about 20 nL, about 30 nL, about 40 nL, about 50 nL, about 60 nL, about 70 nL, about 80 nL, about 90 nL, about 100 nL, about 150 nL, about 200 nL, about 250 nL, about 300 nL, about 400 nL, about 500 nL, about 600 nL, about 700 nL, about 800 nL, about 900 nL, about 1 µL, about 2 µL, about 3 µL, about 4 µL, about 5 µL, about 6 µL, about 7 µL, about 8 µL, about 9 µL, or about 10 µL. In some embodiments, the volume is no more than about 20 µL, about 250 nL, about 200 nL, or about 50 nL. In some embodiments, the volume is no more than about 10 nL, about 20 nL, about 30 nL, about 40 nL, about 50 nL, about 60 nL, about 70 nL, about 80 nL, about 90 nL, about 100 nL, about 150 nL, about 200 nL, about 250 nL, about 300 nL, about 400 nL, about 500 nL, about 600 nL, about 700 nL, about 800 nL, about 900 nL, about 1 µL, about 2 µL, about 3 µL, about 4 µL, about 5 µL, about 6 µL, about 7 µL, about 8 µL, about 9 µL, or about 10 µL.

In some embodiments, the methods further comprise introducing a transfer fluid into the first sample region in order to displace at least a portion of the volume from the first sample region into the second sample region. In some embodiments, the transfer fluid is introduced from a reservoir in fluidic communication with the first sample region. In some embodiments, a pumping mechanism is used push flow from the reservoir at a rate that substantially matches the capillary wicking rate of the microporous substrate. In other embodiments, an air pulse displaces fluid in the first sample region to the second sample region.

In some embodiments, the sample fluid is allowed to incubate with a detection moiety or assay reagent (as non-limiting examples, an antibody or an antigen binding fragment thereof, a biosynthetic antibody binding site including an sFv, aptamer, avibody, peptide, PNA, functionalized nanoparticle or the like.) within the first sample region. In other embodiments, the detection moiety is contained within the microporous substrate or other intermediate layer such as a glass conjugate pad, whereupon the breach of the passive valve introduces the sample fluid to an incubation region on the microporous substrate. In other embodiments, the sample fluid is first flowed over the transduction area of the first or second sample region, followed by rehydration and transport of an upstream detection moiety using fluid from the reservoir.

In some embodiments, the detection substrate comprises a microporous substrate and the fluid flows through the microporous substrate. In some embodiments, the detection substrate comprises a microporous substrate and at least a portion of the volume traverses the microporous substrate. In some embodiments, the microporous substrate has a geometry configured to facilitate a substantially uniform fluid front as at least a portion of the volume traverses the microporous substrate in the direction of flow. In some embodiments, the microporous substrate has an hourglass-shaped geometry. In some embodiments, the microporous substrate geometry has a center serpentine channel surrounded by more linear, shorter path-length hydration channels. In some embodiments, the microporous substrate geometry comprises a plurality of apertures for increasing flow homogenization. In other embodiments, the microporous substrate is shaped to effect preferential rehydration of high resistance areas. In yet other embodiments, the microporous substrate is shaped to allow a hydration flow to move through low resistance or low path length areas while the sample fluid is delayed through higher resistance or higher path length areas.

Disclosed herein, in some embodiments, are methods of treating or monitoring an eye condition in an individual in need thereof comprising: introducing a volume of a tear film sample from the individual into a first sample region of an analysis device; detecting an energy property of the volume within the first sample region using at least one transducer, thereby generating a first sample reading; flowing at least a portion of the volume to a second sample region of the analysis device; detecting one or more analytes in the at least a portion of the volume within the second sample region using a detection substrate, thereby generating a second sample reading; and adjusting a treatment plan for treating the eye condition in the individual, based on the first and second sample reading. In some embodiments, the method further comprises collecting the volume of tear film sample. In some embodiments, the eye condition is keratoconjunctivitis sicca. In some embodiments, the eye condition is allergy. In some embodiments, the eye condition is diabetes. In some embodiments, the eye condition is diabetic retinopathy. In some embodiments, the eye condition is age-related macular degeneration. In some embodiments, the eye condition is glaucoma. In some embodiments, the eye condition is one or more of age-related macular degeneration, allergy, blepharitis, cataracts, conjunctivitis, cellulitis, central serous retinopathy, chalazion, contact lens related damage, corneal/conjunctival abrasions, dystrophies, erosions, lacerations, ulcers, corneal transplant rejection, cytomegalovirus retinitis, diabetic retinopathy, eye cancers, Fuch's dystrophy, Grave's disease, histoplasmosis, glaucoma, infection, keratitis, keratoconus, macular disease, neovascularization, ocular hypertension, optic neuritis, pinguecula, pterygium, retinitis pigmentosa, retinoblastoma, scleritis, trachoma, trichiasis, or uveitis.

As the sample fluid interacts with the microporous substrate, there is a certain rate of nonspecific binding that progressively eliminates signal along the path length through the microporous membrane. Therefore, certain embodiments minimize the interaction of the sample fluid with bare microporous substrate prior to flow over the transducer, in order to eliminate nonspecific losses and reduction in precision. In some embodiments, the geometry of the microporous substrate uses a short wedge or triangle shaped protrusion to serve as the initial interface between sample regions, thereby minimizing the amount of bare membrane the sample fluid interacts with. In some embodiments, the detection moieties are placed within and allowed to incubate with the sample fluid within the collection channel to avoid sample fluid from interacting with bare membrane altogether.

Disclosed herein, in some embodiments, are devices for analyzing a fluidic sample, the device comprising: (a) a fluid inlet; (b) a sample region disposed within the device in fluidic communication with the fluid inlet and shaped to receive a volume of the fluidic sample, the sample region comprising a detection substrate configured to permit detection one or more analytes in the volume to generate a first sample reading; and (c) a fluid reservoir disposed within the device and in fluidic communication with the sample region, the fluid reservoir containing a transfer fluid, which when transferred to the sample region is capable of hydrating a reagent disposed within the sample region, washing the detection substrate during operation of the device, or both. In some embodiments, the device further comprises a metering mechanism that controls fluid flow between the fluid inlet and the sample region. In some embodiments, the metering mechanism comprises a passive valve, or an active valve, or a combination thereof. In some embodiments, the passive valve comprises one or more geometric features that constrain the flow of the volume into the sample region. In some embodiments, the active valve comprises an electrode having a hydrophobic coating and application of a voltage to the electrode causes dissolution of the hydrophobic coating, thereby permitting the flow of the at least a portion of the volume to the sample region. In some embodiments, the hydrophobic coating comprises an alkanethiol self-assembled monolayer. In some embodiments, the device further comprises a second sample region disposed between, and in fluidic communication with, the inlet and the first sample region, wherein the second sample region comprises at least one transducer configured to detect an energy property of the fluidic sample. In some embodiments, the second sample region comprises a capillary channel. In some embodiments, the at least one transducer is situated on a wall of the capillary channel. In some embodiments, the fluidic sample comprises tear fluid. In some embodiments, the first sample reading is indicative of the presence or concentration of the one or more analytes in the fluidic sample. In some embodiments, the second sample reading is indicative of osmolarity of the fluidic sample. In some embodiments, the volume is within a range from about 10 nL to about 10 μL. In some embodiments, the volume is within a range from about 50 nL to about 250 nL. In some embodiments, the volume is no more than 10 nL, 20 nL, 30 nL, 40 nL, 50 nL, 60 nL, 70 nL, 80 nL, 90 nL, 100 nL, 150 nL, 200 nL, 250 nL, 300 nL, 400 nL, 500 nL, 600 nL, 700 nL, 800 nL, 900 nL, 1 μL, 2 μL, 3 μL, 4 μL, 5 μL, 6 μL, 7 μL, 8 μL, 9 μL, or 10 μL. In some embodiments, the detection substrate comprises a microporous substrate, and, during operation, at least a portion of the volume traverses the microporous substrate. In some embodiments, the microporous substrate has a geometry configured to facilitate a substantially uniform fluid front as at least a portion of the volume traverses the microporous substrate in the direction of flow. In some embodiments, the microporous substrate has an hourglass-shaped geometry. In some embodiments, the microporous substrate comprises a plurality of apertures to facilitate the substantially uniform fluid front. In some embodiments, the detection substrate further comprises an immobilized first binder capable of binding, either directly or indirectly, the one or more analytes if present in the volume. In some embodiments, the first binder is selected from the group consisting of an antibody or an antigen binding fragment thereof, a member of an avidin-biotin binding pair, and a member of a streptavidin-biotin binding pair. In some embodiments, the detection substrate further comprises a second binder capable of binding the one or more analytes if present in the volume, wherein the second binder optionally is conjugated with a detectable moiety. In some embodiments, the detectable moiety is a nanoparticle, a visually detectable label, a fluorescent label, or a bioluminescent label.

Disclosed herein, in some embodiments are methods of analyzing a fluidic sample, the method comprising: (a) introducing a volume of the fluidic sample into the sample region of the device of a device provided herein; and (b) detecting the presence and/or concentration of the one or more analytes in the volume, if present in the fluidic sample. In some embodiments, the fluidic sample comprises tear fluid. In some embodiments, the volume is within a range from about 10 nL to about 10 μL. In some embodiments, the volume is within a range from about 50 nL to about 250 nL. In some embodiments, the volume is no more than 10 nL, 20 nL, 30 nL, 40 nL, 50 nL, 60 nL, 70 nL, 80 nL, 90 nL, 100 nL, 150 nL, 200 nL, 250 nL, 300 nL, 400 nL, 500 nL, 600 nL, 700 nL, 800 nL, 900 nL, 1 μL, 2 μL, 3 μL, 4 μL, 5 μL, 6 μL, 7 μL, 8 μL, 9 μL, or 10 μL.

Disclosed herein, in some embodiments, are methods of treating or monitoring an eye condition in an individual, the method comprising: (a) introducing a volume of a tear film sample from the individual into the sample region of a device provided herein; (b) detecting the presence and/or concentration of the one or more analytes in the volume; and (c) adjusting a treatment plan for treating the eye condition in the individual, based on the presence and/or concentration of the one or more analytes in the volume. In some embodiments, the eye condition is keratoconjunctivitis sicca. In some embodiments, the eye condition is allergy. In some embodiments, the eye condition is diabetes. In some embodiments, the eye condition is diabetic retinopathy. In some embodiments, the eye condition is age-related macular degeneration. In some embodiments, the eye condition is glaucoma. In some embodiments, the eye condition is one or more of age-related macular degeneration, allergy, blepharitis, cataracts, conjunctivitis, cellulitis, central serous retinopathy, chalazion, contact lens related damage, corneal/conjunctival abrasions, dystrophies, erosions, lacerations, ulcers, corneal transplant rejection, cytomegalovirus retinitis, diabetic retinopathy, eye cancers, Fuch's dystrophy, Grave's disease, histoplasmosis, glaucoma, infection, keratitis, keratoconus, macular disease, neovascularization, ocular hypertension, optic neuritis, pinguecula, pterygium, retinitis pigmentosa, retinoblastoma, scleritis, trachoma, trichiasis, and uveitis.

Other objects and features of the present invention will become apparent by a review of the specification, claims, and appended figures.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings of which:

DETAILED DESCRIPTION

Figure 1:
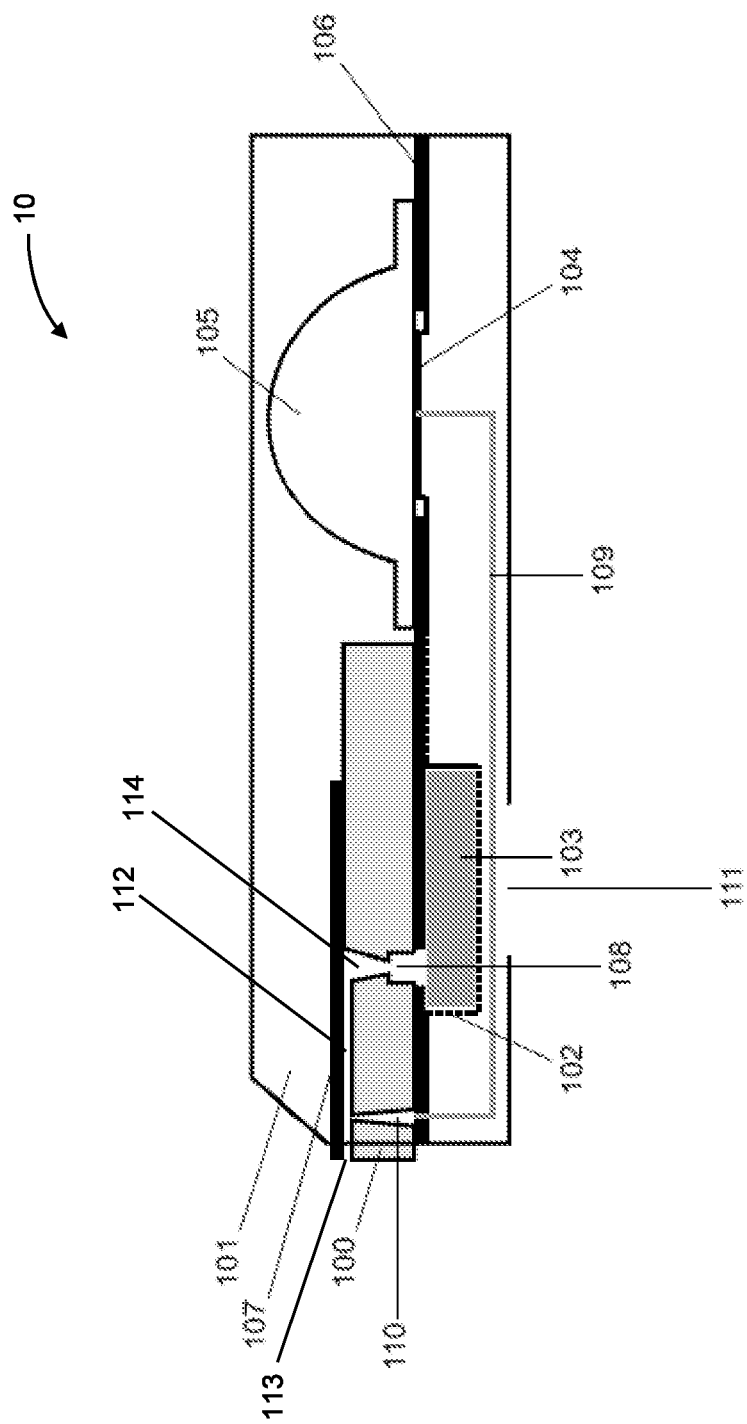
FIG. 1 illustrates a cross-sectional view of a non-limiting exemplary microfluidic device with a passive valve for metering fluid flow, in accordance with some embodiments.

The present disclosure provides, in certain embodiments, systems, methods, and devices for collecting and analyzing small volumes (as a non-limiting example, less than about 20 microliters) of fluidic samples. The systems, methods and devices as disclosed herein are used, in some embodiments, to detect and/or measure one or more features of the sample of fluid of interest. As a non-limiting example, systems, methods and devices are used to measure a first feature (as a non-limiting example, the osmolality of a fluid of interest) and a second feature of interest (as a non-limiting example, the presence and/or concentration of one or more analytes in the fluid of interest). In some embodiments, the systems, methods and devices are used to measure the presence and/or concentration of one or more analytes in a fluid of interest. In some embodiments, the systems, methods and devices are used to measure a first feature (as a non-limiting example, the osmolality of a fluid of interest) or a second feature of interest (as a non-limiting example, the presence and/or concentration of one or more analytes in the fluid of interest).

The present invention addresses problems that can arise when attempting to collect and analyze nanoliter (nL) samples of fluid in an integrated device for use at the point of care. Small volumes of sample have fewer molecules to detect than larger volumes at the same concentration, requiring very high sensitivity. Usually, assays attempt to solve this problem by long incubation times of upwards of an hour up to overnight to allow diffusion to help accumulate analytes of interest at the detector surface, accompanied by repeated, stringent washing to remove nonspecific background. Neither of these techniques is available at the point of care, which requires rapid tests (as a non-limiting example, less than a few minutes) with simple systems operable by entirely untrained users. Additionally, when implementing a serial analysis of both an impedance-based tear osmolarity and a chromatographic type (or lateral flow) sandwich assay, any of a variety issues can arise, such as: accurately metering the collected fluid, rehydration of the detection antibody (or as non-limiting examples including nanoparticle complex, aptamer, scFv, or the like), sample transfer efficiency, achieving rehydration of the capture antibody before the tear sample has fully passed over the sample region, preventing overflow of the running buffer over the microporous lateral flow membrane, homogenizing flow (creating a substantially isotropic, uniform pattern of flow at the leading edge of the detection antibody, or alternatively, wherein the majority of the reacted tear sample and detection complex front flows through the capture region rather than around it), and avoiding flow instabilities that randomly shift flow to one side or the other of the chromatographic system.

To address these issues, the present disclosure provides, in some embodiments, integrated microfluidic collection devices that comprise (a) a substrate that receives an aliquot volume of a sample fluid, wherein the substrate is operatively shaped to receive the aliquot volume of sample fluid through capillary action; and at least one of (b) a sample fluid region of the substrate, sized such that the volume of the sample fluid is sufficient to operatively cover a portion of the sample region, whereupon energy properties of the sample fluid is transduced to produce a sample fluid reading indicating the osmolarity of the sample, and (c) a second sample region that analyzes a portion the sample fluid for analytes of interest. In certain embodiments, the device and system as disclosed herein also contains a series of one or more of balanced passive valves to meter the sample fluid, wherein pressurizing fluid through the system will traverse the valves in a pre-determined sequence. In certain embodiments, the device and system as disclosed herein also contains at least one integrated reservoir. In some embodiments, the reservoir holds a buffer, wash fluid, transfer fluid, sample fluid, gas, air or any other fluidic volume therewithin. In some embodiments, the reservoir is partitioned to hold more than one of a transfer buffer, wash fluid, transfer fluid, sample fluid, gas, air or any other fluidic volume therewithin. Some embodiments feature a second sample region comprising a microporous substrate, operatively shaped to optimize sample transfer efficiency, rehydration dynamics, overflow protection and fluidic resistance balancing to avoid flow instabilities. In certain embodiments, the sample transfer efficiency is optimized by placement of a small protrusion of the microporous substrate into the interface between the two sample regions. In other embodiments, rehydration dynamics of the detection complex are achieved by placing the detection complex of the immunoassay on the metered side of a passive valve, or within the collection channel, or both. In other embodiments, rehydration of the detection complex is achieved within the microporous substrate following sample transfer. In other embodiments, rehydration dynamics of the capture region are achieved by placing downstream fluidic constrictions such that the fluidic path of least resistance passes through the capture region rather than around it. In other embodiments, rehydration of the capture region is achieved downstream of a rapid expansion in the fluidic cross sectional path. In another embodiment, rehydration of the capture region is achieved by patterning one or more serpentine channels within the microporous substrate that acts as a fluidic delay and a preferential path for sample transfer while smaller, shorter path length rehydration channels wick transfer buffer to the downstream capture region prior to the arrival of the delayed sample, at which point the rehydration and sample paths merge. In other embodiments, shorter path length rehydration channels that surround a central sample path focus the developed flow of the detector into a more predictable area after the rehydration channels and sample channels merge into a single path. In other embodiments, one or more fluidic channels are added to help mitigate the possibility of pressure driven overflow from the reservoir. In other embodiments, the rehydration and overflow protection channels are combined into one structure. In an additional embodiment, downstream sample flow resistors are balanced to prevent flow from randomly choosing an asymmetric path through the microporous substrate that creates a flow instability and unpredictability within the system. In other embodiments, asymmetric flow instabilities are allowed in the system and are compensated by placing redundant capture regions on either side of a symmetric path and their intensities averaged in software. Collectively, these features address the problems of parallel analysis of one or more analytes of interest in nanoliter sized samples.

In some embodiments, a volume of a fluidic sample of interest is sequentially and controllably flowed through a plurality of sample regions in a single microfluidic device. In some embodiments, each sample region includes various detection components for analyzing and detecting various properties of the sample volume, such as osmotic pressure, total concentration, osmolality and/or osmolarity, as well as detection of one or more analytes of interest. Some embodiments of the present disclosure are configured to be relatively fast, non-invasive, inexpensive, and/or easy to use, with minimal risk of injury to the patient. Accurate measurements are provided with as little as microliter volumes of a sample fluid, in some embodiments. As a non-limiting example, a measuring device configured in accordance with some embodiments described herein enables osmolarity measurement with no more than 20 microliters of sample fluid. In some embodiments, smaller volumes, as non-limiting examples, nanoliter volumes, sometimes as small as 20 nanoliters, are successfully measured. In some embodiments, measurement performance is not compromised by variations in the volume of sample fluid collected, so that the measurements of osmolarity and the one or more analytes of interest are substantially independent of collected volume. In one embodiment, this is achieved through interrogating a well-defined subset of the aliquot volume of the sample fluid. In some embodiments, the approaches described herein enable the rapid analysis of small sample volumes within a single integrated device, thereby enhancing the speed, flexibility, user convenience, and cost-efficiency of diagnostic testing of fluidic samples.

In some embodiments, the devices described herein are used to analyze a variety of different types of fluids, including tear film, sweat, blood, urine, saliva, or other bodily fluids, or combinations thereof. In some embodiments, the devices described herein are used to analyze other sample fluids, such as milk or other beverages, as well as various buffers, solutions, reagents, or chemicals, or combinations thereof.

In some embodiments, the devices described herein are used to analyze tear fluid from a patient. In some embodiments, tear fluid analysis is beneficial for diagnosing, monitoring, and/or treating various eye conditions in which abnormalities manifest in the patient's tear film. For example, keratoconjunctivitis sicca (KCS), or "dry eye", is a condition in which one or more of the tear film structure components (as a non-limiting example, underlying mucin foundation, middle aqueous component, overlying lipid layer) is present in insufficient volume or is otherwise out of balance with the other components. It is known that the fluid tonicity or osmolarity of tears increases in patients with KCS. KCS is associated with conditions that affect the general health of the body, such as Sjogren's syndrome, aging, and androgen deficiency. Therefore, osmolarity of a tear film is a sensitive and specific indicator for the diagnosis of KCS and other conditions.

In addition, recent evidence has shown that tear hyperosmolarity is directly linked with tear film instability, the condition where the tear film transitions from a homeostatic system in equilibrium with the blood osmolarity, to a progressively more chaotic, unpredictably structured form. In early stages of dry eye disease, the tear film can be metastable, where blink-to-blink variations in strength, lid contact, etc., draw back a variably competent thin film depending on the aforementioned variables. In advanced dry eye disease, or any other ocular surface condition that promotes instability, the tear film is compromised to the point where cohesive forces are insufficient to maintain any semblance of a film, and rapid evaporation over the cornea and conjunctiva results. Such instability is relevant when attempting to measure analytes such as protein biomarkers within a tear film sample. For example, point samples of tear biomarkers (as a non-limiting example, for in vitro diagnostic single use disposable tests that give data on the concentration of a biomarker at the single time point of sample collection) are susceptible to unacceptable variations when making clinical decisions unless the sample osmolarity is accounted for because of the first-order variation in concentration due to tear instability and the resultant hyperosmolarity due to evaporative water loss.

In some embodiments, a plurality of analytes of interest is assayed and used to assist in the diagnosis and management of one or more eye diseases. Non-limiting examples of eye diseases include: age-related macular degeneration, allergy, blepharitis, cataracts, conjunctivitis, cellulitis, central serous retinopathy, chalazion, contact lens related damage, corneal/conjunctival abrasions, dystrophies, erosions, lacerations, ulcers, corneal transplant rejection, cytomegalovirus retinitis, diabetic retinopathy, eye cancers, Fuch's dystrophy, Grave's disease, histoplasmosis, glaucoma, infection, keratitis, keratoconus, macular disease, neovascularization, ocular hypertension, optic neuritis, pinguecula, pterygium, retinitis pigmentosa, retinoblastoma, scleritis, trachoma, trichiasis, and uveitis. In some embodiments, a parallel interpretation (as a non-limiting example, a logical OR, where if any of the plurality of analytes is positive, returns a positive diagnosis) of specific analytes (and/or fluid properties such as osmolarity) are used to increase overall sensitivity of an eye disease test without sacrificing much specificity. As a non-limiting example, in one embodiment, parallel interpretation of osmolarity, lactoferrin, albumin, and lipocalin is used to diagnose dry eye disease. In another embodiment, parallel interpretation of osmolarity, lipocalin, proline-rich protein 4 (PRR4) and zinc-alpha-2-glycoprotein 2 (ZAG2) (or other major tear proteins) is used to diagnose dry eye disease when the protein levels are lower than their normal range. In yet another embodiment, parallel interpretation of osmolarity, lipocalin, PRR4 and ZAG2 (or other major tear proteins) is used to diagnose naïve untreated glaucoma if the levels are higher than the normal range. In yet another embodiment, parallel interpretation of osmolarity, lipocalin, PRR4 and ZAG2 (or other major tear proteins) is used to diagnose both dry eye and glaucoma in the same device. In some embodiments, parallel interpretation of osmolarity and glycated albumin enable an increased precision in the differentiation between healthy patients, diabetic patients, and diabetic patients with retinopathy, by compensating for the blink-to-blink variation in tear concentration by normalizing the glycated albumin concentration against the measured osmolarity. In yet other embodiments, parallel interpretation of osmolarity and brain-derived neurotrophic factor (BDNF) allows improved precision into the determination of low tension glaucoma by normalizing the BDNF level against the measured tear osmolarity. In another embodiment, parallel interpretation of osmolarity, IL-1Ra, MMP-9 and S100A8 helps diagnose both dry eye disease and the causative subsets of the disorder, whether inflammatory or aqueous deficiency. In other embodiments, multiple analytes of interest from different diseases with overlapping symptoms and clinical presentation are measured in parallel. As a non-limiting example, in one embodiment, osmolarity plus a plurality of allergy markers such as IgE, ECP and/or EDN are measured to interrogate both early and late stage allergy while differentiating between dry eye and allergy despite similar clinical presentation and symptoms. In other embodiments, osmolarity is not measured, while the analytes of interest are. These examples are not meant to be limiting, but do provide examples of how to apply the disclosed devices at the point-of-care.

Accordingly, the present disclosure provides, in some embodiments, systems, methods, and devices for measuring the osmolarity of an aliquot volume (as a non-limiting example, of a tear film or other fluidic sample) in conjunction with measuring one or more analytes of interest in the volume (as a non-limiting example, the presence and/or concentration of one or more analytes). In some embodiments, the osmolarity and analyte measurements are performed simultaneously or sequentially. In some embodiments, the osmolarity measurement is performed first, followed by an assay to detect the presence and/or concentration of one or more analytes in the sample volume. In some embodiments, the osmolarity measurement is performed second, following an assay to detect the presence and/or concentration of one or more analytes in the sample volume. In other embodiments, the osmolarity of the sample is relatively constant and only analytes of interest are assayed.

In some embodiments, any suitable technique is used to measure the osmolarity of a fluidic sample. In some embodiments, the osmolarity is measured by detecting energy properties of the sample (as a non-limiting example, thermal, optical, and/or electrical properties), such as by transferring energy to the sample, detecting the imparted energy, and using the detection result to determine osmolarity. In some embodiments, one or more transducers or electrodes are used to measure the electrical conductivity of the fluid, as a non-limiting example, by applying a suitable electrical signal. Since the electrical conductivity is related to the ion concentration of the fluid, the osmolarity of the fluid is able to be determined if temperature correction and appropriate calibration functions are applied.

Analytes that are able to be measured in a fluidic sample using the techniques, systems and devices presented herein include, but are not limited to proteins, peptides, metabolites, electrolytes, small molecules, lipids, sugars, nucleic acids and proteoglycans, amongst other biological moieties and higher order assemblies, as well as combinations thereof. In some embodiments, the analytes include protein biomarkers. In some embodiments, the analytes include but are not limited to: immunoglobulins (as a non-limiting example, Immunoglobulin E (IgE), Immunoglobulin M (IgM), Immunoglobulin A (IgA), Immunoglobulin G (IgG)), cytokines (as a non-limiting example, transforming growth factor-β(TGF-β), Tumor necrosis factors (TNF-α), Interleukin 1-A), proteins (S100, lactoferrin, lipocalin, cathepsin, BDNF, enolase, Eosinophil Cationic Protein (ECP), Eosinophil Derived Neurotoxin (EDN), PRR4, ZAG2, cystatin, albumin, or the like) or mucins and other glycoproteins (as a non-limiting example, cell surface associated mucin 5 (MUC-5), proteoglycan 4 (PRG4), cell surface associated mucin 16 (MUC16)). In some embodiments, the analyte detection and/or measurement procedure involves flowing the fluidic sample through a detection substrate. Non-limiting exemplary detection substrate includes a microporous substrate or microporous membrane. In further embodiments, the detection substrate is one or more selected from nitrocellulose, glass fiber conjugate pads, Fusion 5, POREX® materials, paper, PVDF, or the like. In some embodiments, the microporous substrate and the microporous membrane are equivalent and interchangeable herewithin. In some embodiments, the collection channel, the capillary channel, and the microfluidic channel are equivalent terms and interchangeable herewithin. In some embodiments, the detection substrate is configured for chromatographic, flow through, or lateral flow analysis of one or more analytes of interest. Other non-limiting exemplary techniques include impedance, impedance spectroscopy, surface-enhanced Raman spectroscopy (SERS), electrochemical transducers, label-free transducers such as surface plasmon resonance, interferometry, or the like. Assays for detecting analytes in a fluid volume are known to those of skill in the art and are described in further detail below.

In some embodiments, the systems, methods, and devices provided herein are applied to the analysis of osmolarity and analyte concentration in relatively small volumes of fluidic samples, such as a volume within a range from about 10 nL to about 10 µL, or within a range from about 50 nL to 250 nL. In some embodiments, the volume is within a range between any two of the following: about 10 nL, about 20 nL, about 30 nL, about 40 nL, about 50 nL, about 60 nL, about 70 nL, about 80 nL, about 90 nL, about 100 nL, about 150 nL, about 200 nL, about 250 nL, about 300 nL, about 400 nL, about 500 nL, about 600 nL, about 700 nL, about 800 nL, about 900 nL, about 1 µL, about 2 µL, about 3 µL, about 4 µL, about 5 µL, about 6 µL, about 7 µL, about 8 µL, about 9 µL, or about 10 µL. In some embodiments, the volume is no more than about 20 µL, about 250 nL, about 200 nL, or about 50 nL. In some embodiments, the volume is no more than about 10 nL, about 20 nL, about 30 nL, about 40 nL, about 50 nL, about 60 nL, about 70 nL, about 80 nL, about 90 nL, about 100 nL, about 150 nL, about 200 nL, about 250 nL, about 300 nL, about 400 nL, about 500 nL, about 600 nL, about 700 nL, about 800 nL, about 900 nL, about 1 µL, about 2 µL, about 3 µL, about 4 µL, about 5 µL, about 6 µL, about 7 µL, about 8 µL, about 9 µL, or about 10 µL.

In some embodiments, the osmolarity and analyte measurements are performed in a single microfluidic device, such a microfluidic chip. In some embodiments, the microfluidic device includes a plurality of sample regions shaped to receive a volume of the fluidic sample, as a non-limiting example, microfluidic channels, chambers, and the like. In some embodiments, the dimensions of the microfluidic structures are varied as desired. In some embodiments, the microfluidic channels, the assay channels, or the overflow channels as described herein have a channel width of about 10 µm, about 20 µm, about 30 µm, about 40 µm, about 50 µm, about 60 jam, about 70 µm, about 80 µm, about 90 µm, about 100 µm, about 200 µm, about 300 µm, about 400 µm, about 500 µm, about 600 µm, about 700 µm, about 800 µm, about 900 µm, or about 1 mm. In some embodiments, the channel depth or height is about 5 µm, about 10 µm, about 20 µm, about 30 µm, about 40 µm, about 50 µm, about 60 µm, about 70 µm, about 80 µm, about 90 µm, about 100 µm, about 1500 µm, about 200 µm, about 250 µm, about 300 µm, or about 400 µm. In some embodiments, the devices described herein include a capillary channel for performing osmolarity detection on a sample volume that has a channel width of about 300 µm and a channel depth of about 75 µm. In some embodiments, the channel width is the largest distance connecting two spatial points of a cross-sectional contour of the channel.

In some embodiments, each of the sample regions of the microfluidic device is used to perform a different analytical function. In some embodiments, the device includes a first sample region including at least one transducer for measuring osmolarity and a second sample region including a detection substrate for performing analyte detection. In embodiments where the osmolarity and analyte measurement are performed sequentially (as a non-limiting example, osmolarity detection is performed prior to analyte detection), the sample regions are in fluidic communication with each other (as a non-limiting example, connected by passages, through holes, or other fluidic elements) so as to enable flow of the sample volume from the first sample region into the second sample region. In some embodiments, the flow is actuated by various methods, including but not limited to convective flow, pressure-driven flow, wicking, capillary action, evaporation, dissolution, or suitable combinations thereof. In some embodiments, a second fluid such as a wash fluid is introduced into the microfluidic device in order to displace the sample volume and actuate flow through the system. In some embodiments, the fluidic flow of a sample travels from one of the first and the second sample regions and then to the other sample region of the first and the second sample regions.

In some embodiments, it is beneficial to control the timing and/or rate of flow between the different sample regions of the microfluidic device, as a non-limiting example, in order to ensure sufficient time for performing measurements and to facilitate sample processing. In some embodiments, an osmolarity measurement requires approximately 1-2 seconds to perform. In other embodiments of the device, an osmolarity measurement requires approximately 3-10 seconds to perform after the system waits for transient flow dynamics to settle. Accordingly, some embodiments of the microfluidic devices described herein incorporate one or more metering mechanisms or other flow control elements in order to ensure that the sample volume is retained in the sample region for an appropriate length of time and to prevent premature flow of the sample volume into other regions.

In a particular embodiment, FIG. 1 illustrates a cross-sectional view of a microfluidic device 10 for integrated detection of osmolarity and analytes of interest having a passive valve as a metering mechanism, in accordance with some embodiments. In the embodiment of FIG. 1, the microfluidic capillary chip 100 is integrated into the interior of a microfluidic capsule 101 that provides a convenient way to protect the contents in the interior during handling. The capsule 101 includes an interior surface (indicated by dashed line 102) defining a cavity that receives one or more detection substrates 103 (as a non-limiting example, microporous substrates such as nitrocellulose, glass fiber conjugate pads, Fusion 5, Porex materials, paper, PVDF, or the like.) and allows the substrates to be layered vertically during assembly. In some embodiments, the capsule interior contains raised features 104 that allow a reservoir of transfer fluid 105 (as a non-limiting example, a blister pack) to burst when pressed, as described in further detail below. Pressure sensitive adhesive 106 lays down atop the interior surface 102 of the capsule and binds the microporous substrate to both the capsule 101 and the microfluidic capillary chip 100, which is sealed by a hydrophilic pressure sensitive adhesive 107. In some embodiments, a capillary channel 112 is defined between the pressure sensitive adhesive 107 and the upper surface of the microfluidic chip 100, such that the adhesive 107 serves one wall of the channel 112 and the upper surface of the chip 100 serves as a second wall.

In some embodiments, the capillary channel 112 serves as a first sample region in which osmolarity measurements are performed and the cavity containing the detection substrate 103 serves the second sample region in which analyte measurements are performed. In some embodiments, the first and second sample regions of the device 10 are connected to each other by a continuous passage or through-hole 114. In some embodiments, the passage 114 includes a passive valve 108 which serves as a metering mechanism for controlling flow between the two sample regions. For instance, the passive valve 108 includes one or more geometric features used to constrain fluid flow. In some embodiments, the passive valve comprises a sharp change in sidewall angle along a fluidic path, or a modulation of hydrophilicity such as a stripe or region of substantially hydrophobic material atop a generally hydrophilic layer. In a particular embodiment as in FIG. 1, a sharp transition angle in the valve geometry provides a metering function for the sample volumes.

When a fluidic sample volume is introduced into the device 10 via at the inlet 113 of the microfluidic chip 100, it will flow through the channel 112 until it is stopped by the passive valve 108. In some embodiments, the osmolarity of the volume is then determined in the channel 112 using one or more transducers situated in the channel 112. In some embodiments, electrodes (not shown) are embedded within the channel 112 (as a non-limiting example, on the channel wall defined by the chip 100). In some embodiments, the electrodes are patterned onto the surface of the chip 100, such as by metal evaporation and subsequent laser ablation, and are used to determine when sufficient sample fluid has been collected in the channel 112. Additionally, in some embodiments, the electrodes in the capillary channel 112 create an impedance-based transducer, such that energy properties of the sample volume is detected from within the capillary channel 112 to produce a sample reading indicative of the osmolarity of the sample fluid.

In some embodiments, once the sample osmolarity has been measured, the sample volume is displaced from the first sample region (the channel 112) into the second sample region in order to perform analyte measurements. Any suitable technique is used in order to achieve this displacement of the fluidic volume. In some embodiments, the reservoir 105 is externally pressed by an actuating force (as a non-limiting example, by a thumb or another finger, a screw, a fixed feature protruding in a reader system slot, or other actuating element.). This force allows the transfer fluid to flow through capsule microfluidics 109 and into a vertical inlet (which, in some embodiments, is comprised of an additional passive valve) 110 in the chip 100, as a non-limiting example, by pressure-driven flow and/or wicking. In some embodiments, the introduction of the wash fluid (as a non-limiting example, about 1 µL to about 50 µL volume) into the first sample region causes the sample volume to pass through the passive valve 108 and onto the sample region containing the microporous detection substrate 103. In some embodiments, the inlet 113 or the vertical inlet 110 includes one or more unidirectional valve. In some embodiments, the one or more valves are driven by fluidic pressure.

In some embodiments, as the sample flows towards the distal end of the detection substrate 103 (as a non-limiting example, the right side of the detection substrate 103 as depicted in FIG. 1), the sample interacts with assay reagents disposed on or in detection substrate 103 so as to generate a sample reading indicative of the concentration of one or more analytes in the sample fluid. In some embodiments, at least a portion of the detection substrate 103 is exposed via a window 111 in the capsule 101, thereby permitting optical interrogation of the analyte assay results. In other embodiments, chip 100 and the reservoir 105 are assembled onto a separate carrier that is then snapped into or otherwise attached to the capsule. In such an embodiment, the separate carrier provides microfluidic channels that allow fluidic communication to flow from the reservoir 105, to the vertical inlet 110, through the channel 112, up through passage 114 and passive valve 108, and onto the detection substrate 103 rather than the capsule plastics.

Figure 2:
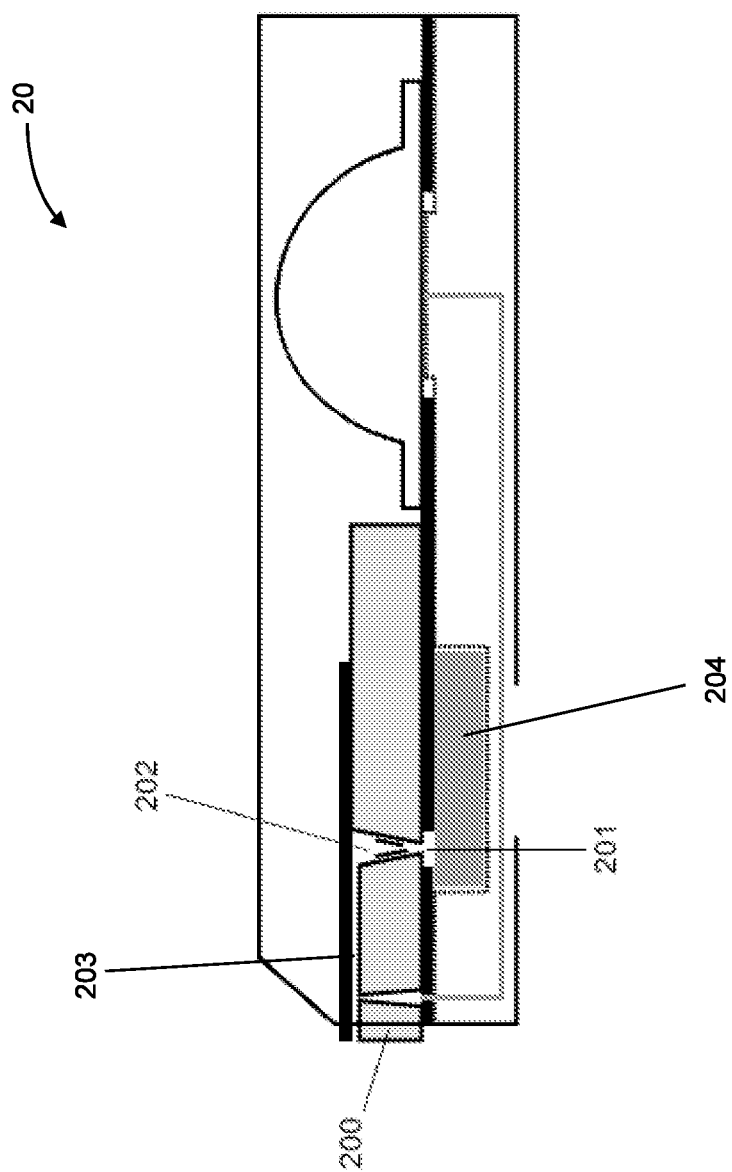
FIG. 2 illustrates a cross-sectional view of a non-limiting exemplary microfluidic device with an active valve for metering fluid flow, in accordance with some embodiments.

In a particular embodiment, FIG. 2 illustrates a cross-sectional view of a microfluidic device 20 for integrated detection of osmolarity and analytes of interest having an active valve as a metering mechanism, in accordance with some embodiments. The components of the device 20 are generally similar to those of device 10, except that the device 20 includes an active valve as a metering mechanism for controlling fluid flow, rather than a passive valve. In the embodiment of FIG. 2, the microfluidic capillary chip 200 includes an active valve composed of active elements 202 that constrain and/or arrest fluid flow between the first sample region (capillary channel 203) and the second sample region (detection substrate 204). In some embodiments, the active elements 202 are located within the through hole 201, or within the capillary channel 203.

Any suitable type of active valve is used to control fluid flow within the device 20. As a non-limiting example, the active valve includes elements that physically obstruct flow between the first and second sample regions, but is displaced upon application of a stimulus or signal in order to permit flow. As another example, the active valve includes surface energy modulating features that interact with the sample fluid so as to reduce or prevent substantial fluid flow. As a non-limiting example, the active elements 202 include one or more electrodes having a hydrophobic coating that impedes fluid flow, such as an alkanethiol surface assembled monolayer (SAM). For instance, an electric field is applied to the electrodes in order to cause electrodissolution of the surface monolayer of alkanethiol groups, thereby transitioning the surface energy and allowing fluid to pass at the selected time. The applied voltage is within a range from about 1V to about 100 V range, such as within a range from about 1V to about 10 V. Other types of active elements 202 that are capable of undergoing a hydrophobic to hydrophilic transition in response to a stimulus are used in other embodiments.

In some embodiments, the surface energy modulating features are designed to dissolve upon exposure to the sample fluid, thereby enabling passage through the valve once sufficient time has elapsed for dissolution. As a non-limiting example, the active elements 202 arrest flow for approximately 1-30 seconds before dissolving and allowing fluid to flow freely to the downstream second sample region. Optionally, the device 20 includes additional microchannels that act as vents to allow air to escape while fluid flows. These microchannel vents are fabricated from hydrophobic materials or include hydrophobic surface coatings so as to prevent fluid from entering into the vents.

Figure 3A:
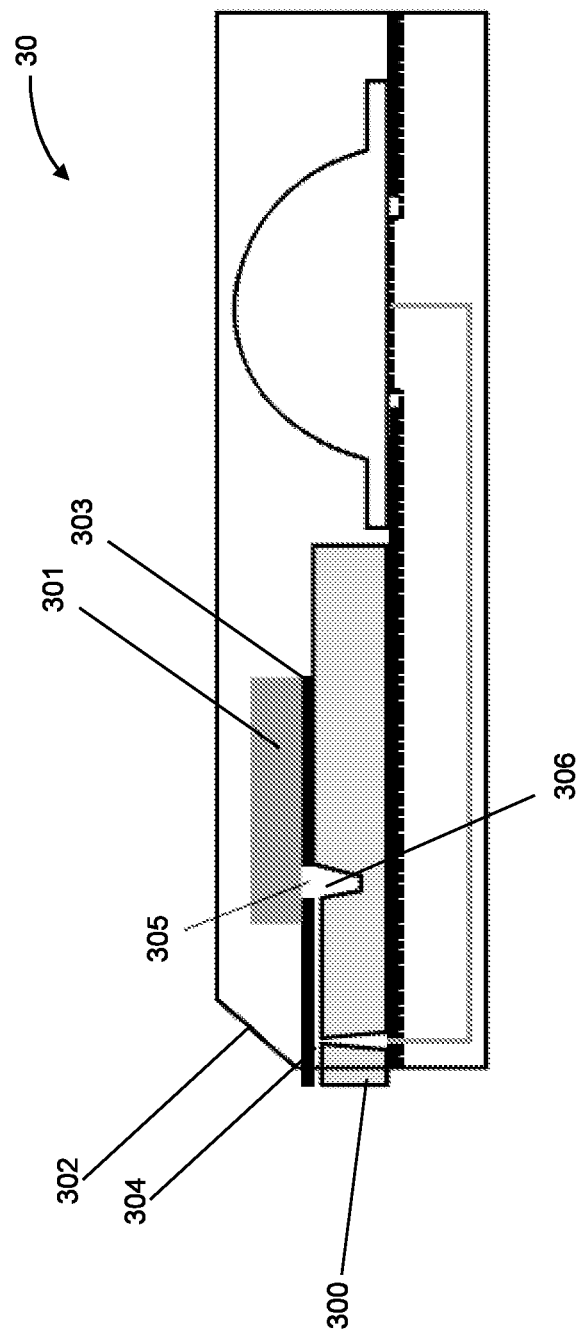
FIG. 3A illustrates a cross-sectional view of a non-limiting exemplary microfluidic device for integrated detection of osmolarity and one or more analytes of interest that utilizes surface energy interactions to delay fluid flow, in accordance with some embodiments.

In a particular embodiment, FIG. 3A illustrates a cross-sectional view of a microfluidic device 30 for integrated detection of osmolarity and analytes of interest that utilizes surface energy interactions to delay fluid flow, in accordance with some embodiments. The components of the microfluidic device 30 are generally similar to those of the devices 10 and 20 except as specified below. Similar to the devices 10 and 20, the device 30 includes a microfluidic capillary chip 300 and detection substrate 301 within a microfluidic capsule 302. In some embodiments, the chip 300 and substrate 301 are sealed and bound to each other by a layer of pressure sensitive adhesive 303. Notably, the detection substrate 301 is positioned on top of the microfluidic chip 300, rather than below as in the devices 10 and 20. A capillary channel 304 is defined by the upper surface of the chip 300 and the layer of pressure sensitive adhesive 303. In some embodiments, chip and the reservoir are assembled onto a separate carrier that is then snapped into or otherwise attached to the capsule. In such an embodiment, the separate carrier provides microfluidic channels that allow fluidic communication to flow from the reservoir, to the vertical inlet, through the channel, up through the passage and passive valve, and onto the detection substrate rather than the capsule plastics. In certain embodiments, the carrier contains a microfluidic reservoir to delay flow or provide fluidic capacitance for trapping bubbles after the initial bursting of the main reservoir.

In some embodiments, the channel 304 serve as a first sample region for performing osmolarity measurements of the sample volume, while the detection substrate 301 serves as the second sample region for analyte detection, similar to the other embodiments described herein. The first and second sample regions are fluidically coupled via a through-hole or passage 305 formed in the layer of pressure sensitive adhesive 303 above an opening 306 in the chip substrate. In some embodiments, the passage 305 and capillary channel 304 do not include any valves or other metering mechanisms for constraining fluid flow. Instead, the device 30 utilizes surface energy interactions of the fluidic sample volume with the adhesive layer 303 to control fluid flow between the first and second sample regions. In some embodiments, the hydrophilicity and/or hydrophobicity of the adhesive layer 303 is tuned as desired in order to achieve control over the fluid flow. As a non-limiting example, the adhesive layer 303 includes a hydrophobic inner layer (as a non-limiting example, a 75 μm PET layer) situated between two hydrophilic outer layers (as a non-limiting example, 25 μm layers). In some embodiments, this multilayered adhesive material slows the flow of the sample volume through the channel 304 so as to allow sufficient time for measuring osmolarity in the channel 304 and delay the sample from entering the detection substrate 301 in the second sample region. As with other embodiments in FIG. 1 and FIG. 2, reaction components for half of a sandwich ELISA are dried, spotted and otherwise immobilized (covalently, ionically, hydrophobically, nonspecifically, adsorbed) in channel 304, in some embodiments. In other embodiments, reaction components for half of a sandwich ELISA are dried, spotted or otherwise immobilized (covalently, ionically, hydrophobically, nonspecifically, adsorbed) into the opening 306. In yet other embodiments, reaction components for half of a sandwich ELISA are dried, spotted or otherwise immobilized (covalently, ionically, hydrophobically, nonspecifically, adsorbed) onto the substrate 301. In some embodiments, such reaction components comprise antibodies or antigen binding fragments thereof, biosynthetic antibody binding sites, aptamers, short chain fragment variables, and the like. In certain embodiments, the second half of a sandwich ELISA is dried, spotted or otherwise immobilized (covalently, ionically, hydrophobically, nonspecifically) within channel 304, opening 306, or substrate 301. Appropriate labels such as fluorescent dyes, nanoparticles, enzymes, electrochemiluminescent, chemiluminescent, HCR, luminescent nanospheres, reflective nanoparticles, redox labels, streptavidin, avidin, neutravidin, biotin, europium chelated dyes, upconverting phosphors, FRET systems, plasmonic labels, etc. accompany the detection half of the sandwich ELISA, in some embodiments.

Non-limiting exemplary reagents, substrate configurations, and methods for making and using substrates to detect the presence and/or concentration of analytes of interest are found in, for example, U.S. Pat. Nos. 6,319,676; 5,141,850; 5,602,040; 5,656,503; 5,714,389; 5,591,645; 5,989,921; 6,319,676; 6,485,982; 7,763,454; and published U.S. Patent Application No. US2015/0017068. U.S. Pat. Nos. 5,714,389; 5,989,921 and 6,485,982 describe assay substrates where an analyte of interest is captured directly in a test region via an immobilized binder for the analyte (as a non-limiting example, an anti-analyte antibody) immobilized in the test region. In this approach, analyte bound to a labeled second binder for analyte (as a non-limiting example, a second anti-analyte antibody) in the form of a "half sandwich" is bound in the test region. U.S. Pat. Nos. 6,319,676 and 5,141,850 describe assay substrates where an analyte of interest is captured indirectly in the test region via an immobilized binder (as a non-limiting example, avidin or strepatavidin) that binds to a binder partner (biotin) covalently coupled to a binder for the analyte of interest (as a non-limiting example, an anti-analyte antibody). In this approach, a "full sandwich" comprising a complex of a capturable binding moiety (as a non-limiting example, a biotinylated anti-analyte antibody)—analyte—detectable binding moiety (as a non-limiting example, a labeled anti-analyte antibody) is formed as fluid traverses the substrate and is then captured in the test region via a binding moiety (as a non-limiting example, avidin or streptavidin) that binds the capturable binding moiety.

In another embodiment, the device is configured for analyzing a fluidic sample, comprising a housing defining a fluid inlet; a sample processing region disposed within the housing in fluidic communication with the fluid inlet and shaped to receive a volume of the fluidic sample, the sample processing region comprising a detection substrate configured to permit detection one or more analytes in the volume to generate a first sample reading; and a fluid reservoir disposed within the housing and in fluidic communication with the sample processing region, the fluid reservoir containing a fluid, which when transferred to the sample processing region is capable of hydrating a reagent disposed within the sample processing region and/or washing the detection substrate during operation of the device.

In various embodiments, device 10, 20 or 30 in FIGS. 1, 2 and-3A omits the first sample region and only contains the second sample region, as a non-limiting example, when the detection of an analyte and/or measurement of the concentration of one or more analyte is desired. In these embodiments, the second sample region is referred to as a sample processing region. In some embodiments, the device as disclosed herein includes only the second sample region. In further embodiments, the sample volume to be examined is directly driven from an inlet and/or a vertical inlet to the second sample region before traveling to the first sample region. In alternative embodiments, the sample volume travels to the first sample region and then to the second sample region.

Figure 3B:
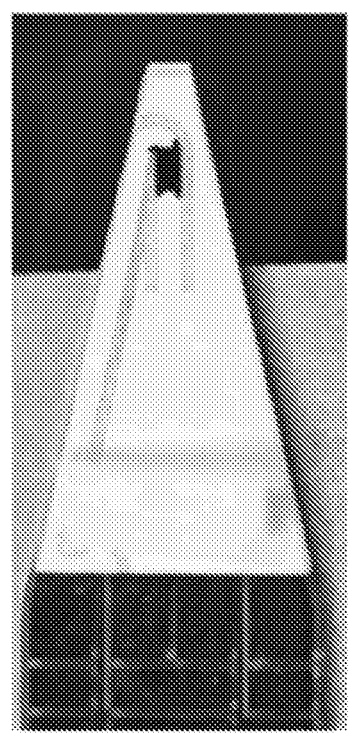
FIGS. 3B and 3C illustrate non-limiting exemplary flow results obtained using a microfluidic device implementing a surface energy-based flow delay mechanism, in accordance with some embodiments.
Figure 3C:
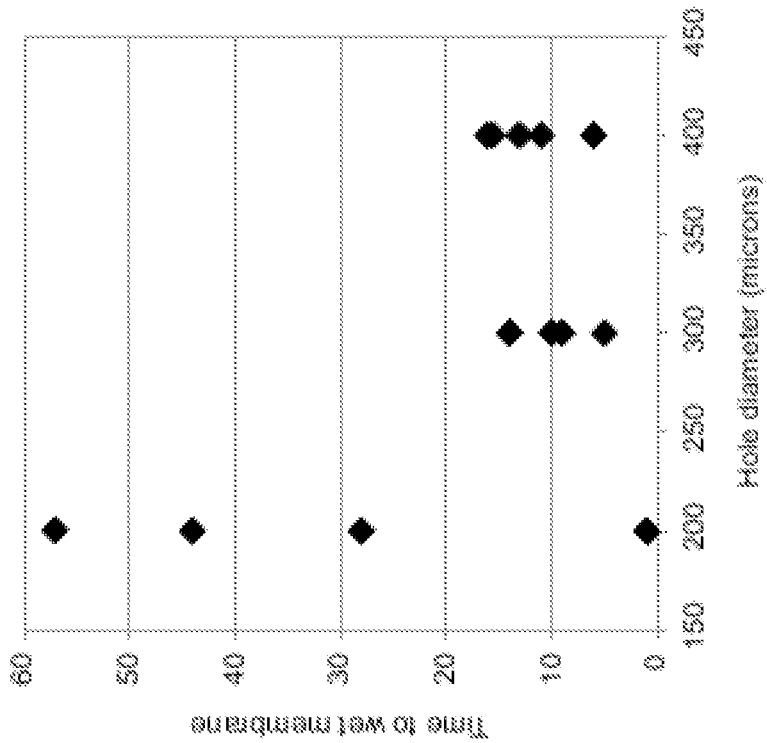

In a particular embodiment, FIGS. 3B and 3C illustrate exemplary flow results obtained using a microfluidic device implementing a surface energy-based flow delay mechanism, similar to the device 30 of FIG. 3A. FIG. 3B illustrates delayed flow of a sample fluid containing red food dye into a microporous membrane (a patterned nitrocellulose membrane) acting as the second sample region. Such a structure enables capillary flow to drive the downstream reaction, as pressure driven flow is taken up by the large paper area, wicked down the side channel of the membrane, then loop around to run a chromatographic assay. FIG. 3C is a graph illustrating the relationship between through-hole diameter and delay time before wetting the microporous substrate. When the hole diameter is 200 µm, a high amount of variability in delay time is observed, ranging from approximately 0 seconds to approximately 60 seconds. However, the variability is lower for devices with 300 µm and 400 µm hole diameters, which exhibit delay times of approximately 10 seconds. In the embodiment of FIG. 3B, the chip substrate opening is approximately 300 µm in diameter, which suggests that the ideal ratio for the pressure sensitive adhesive through-hole diameter to chip substrate opening diameter to a range from about 0.5:1 to about 2:1.

Figure 4A:
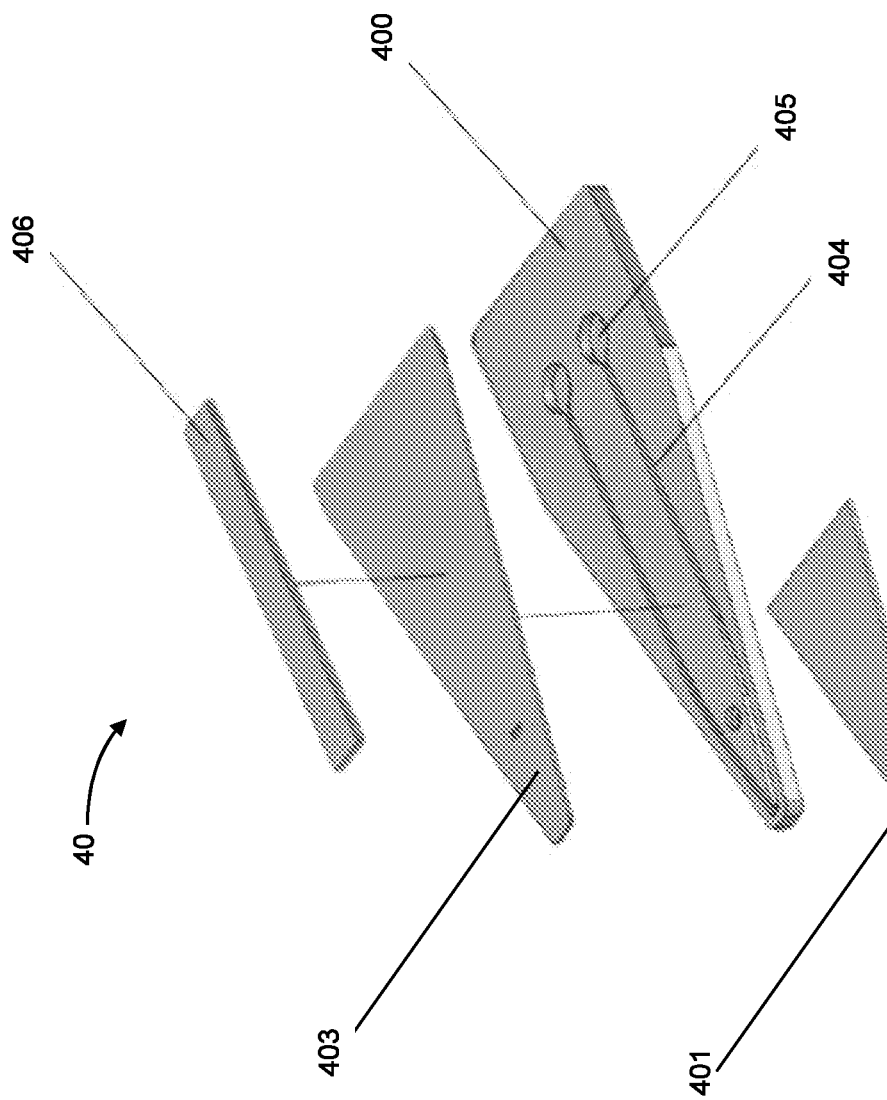
FIG. 4A illustrates an exploded view of a non-limiting exemplary microfluidic device for integrated detection of osmolarity and detection of one or more analytes having a passive valve, in accordance with some embodiments.
Figure 4B:
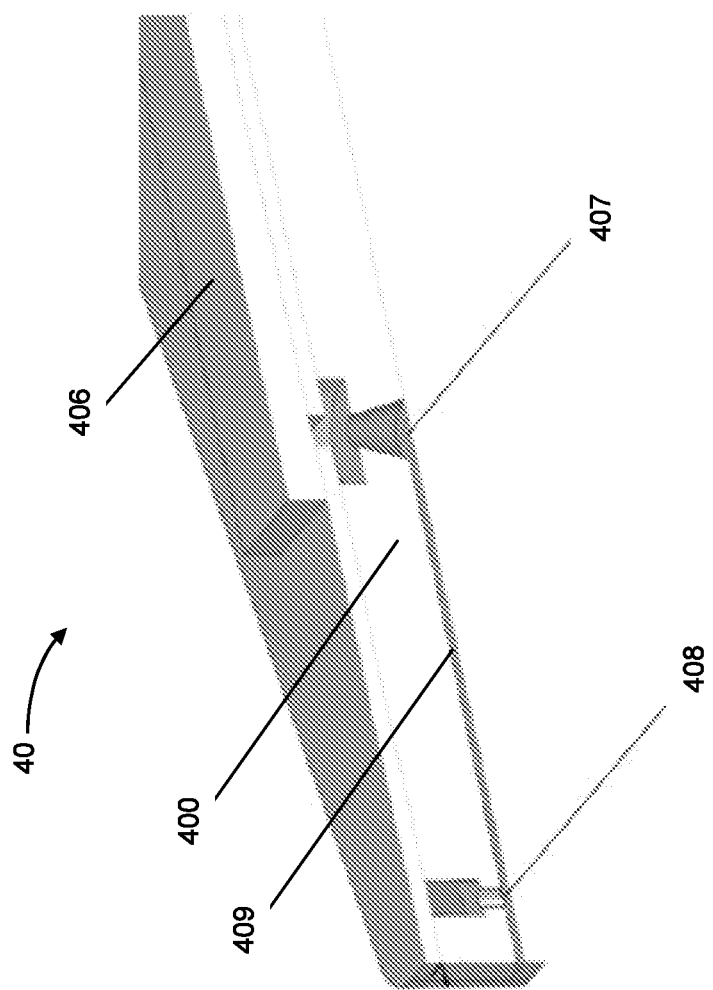
FIG. 4B illustrates a cross-sectional view of the assembled microfluidic device of FIG. 4A.

In a particular embodiment, FIGS. 4A and 4B illustrate a microfluidic device 40 for integrated detection of osmolarity and analytes of interest having a passive valve, in accordance with some embodiments. In the embodiment of FIG. 4A, which illustrates an exploded view of the device 40, the microfluidic capillary chip 400 is assembled in layers with a hydrophilic pressure sensitive adhesive 401 forming one surface of the bottom capillary channel, a double-sided pressure sensitive adhesive layer 403 sealing the microfluidics 404 on the upper surface of the chip 400. The double-sided layer 403 extends up to the fluidic inlet and air outlet ports 405, which accept wash fluid and allow air to escape, respectively. A detection substrate 406 (as a non-limiting example, a microporous membrane or substrate), which acts as the second sample region, is press-sealed against the double-sided pressure sensitive adhesive 403. FIG. 4B shows a cross-sectional view of the assembled microfluidic device 40, in which details of the passive valve 407, fluid inlet 408, and capillary channel 409 are visible. In some embodiments, the capillary channel 409 serves as the first sample region for analyzing osmolarity, and the detection substrate 406 serves as the second sample region for detecting one or more analytes of interest. In some embodiments, a sample volume is collected into the capillary channel 409 of the first sample region and constrained from flowing into the second sample region by the passive valve 407 via the mechanisms discussed above. In some embodiments, upon introduction of wash fluid into the channel 409 via the wash inlet 408, the sample volume is displaced from the channel 409 and into the detection substrate 406 of the second sample region.

Figure 5A:
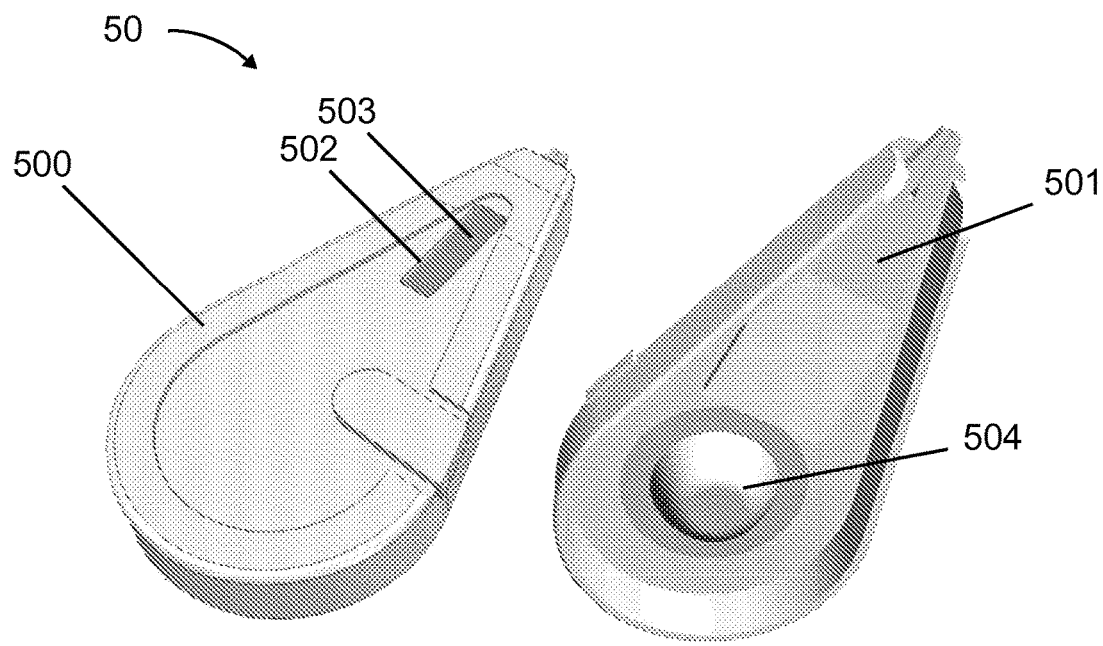
FIG. 5A and FIG. 5B illustrates top and bottom views of an assembled non-limiting exemplary microfluidic devices for integrated detection of osmolarity and one or more analytes of interest, in accordance with some embodiments.
Figure 5B:
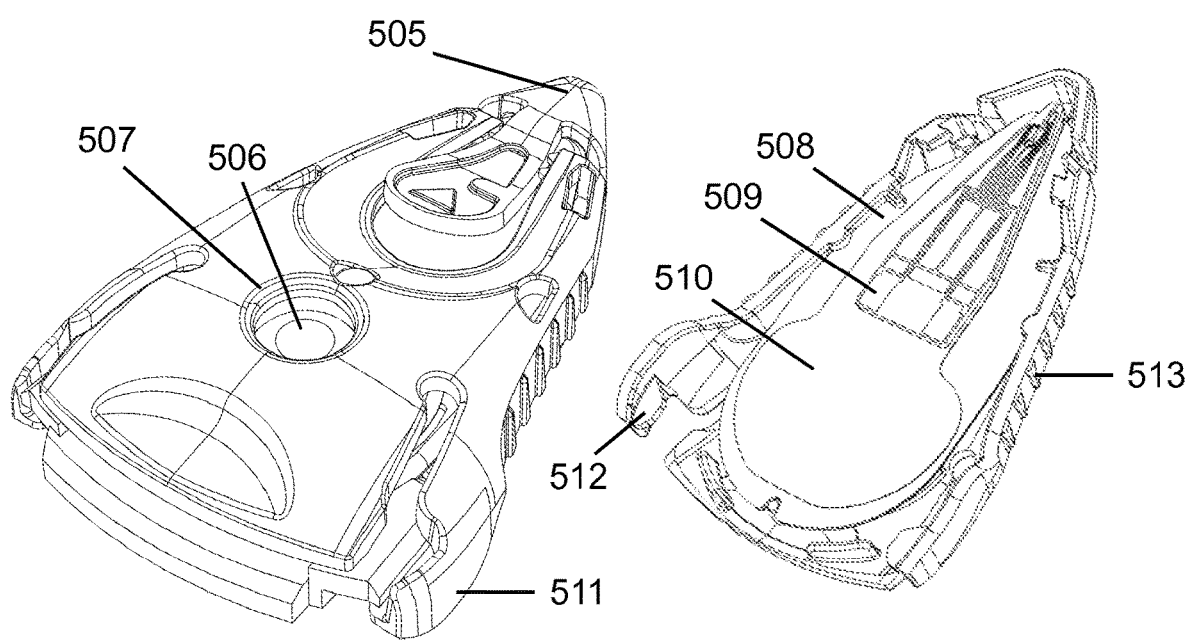

In a particular embodiment, FIG. 5A illustrates a top view (left) and bottom view (right) of an assembled microfluidic device 50 for integrated detection of osmolarity and analytes of interest, in accordance with some embodiments. Similar to the other embodiments provided herein, the device 50 includes a microfluidic capsule 500 and microfluidic chip 501. The capsule 500 includes a window 502 through which a portion of the detection substrate 503 (as a non-limiting example, a microporous substrate) is visible. In some embodiments, the substrate 503 is arranged such that the readout of a lateral flow assay or other analyte detection assay is observed through the window 502 (as a non-limiting example, by a user or a detection device such as a reader system). In some embodiments, the device 50 is also include a fluid reservoir 504 (as a non-limiting example, a blister pack containing a fluidic volume that is used, as non-limiting examples, as a transfer fluid, wash fluid, and/or a hydration fluid) that is mechanically actuated to release a fluidic volume for displacing fluidic sample being tested from the capillary channels of the microfluidic chip 501 to the detection substrate 503, as previously described. In the embodiment of FIG. 5A, the outer surface of blister pack is exposed. In some embodiments, the blister pack is substantially covered except for a small hole to permit actuation. In some embodiments, a configuration of the blister pack is used to prevent a user from accessing the blister pack so as to minimize the potential for accidental actuation and rupture. FIG. 5B shows an embodiment of an assembled microfluidic device for the combined detection of osmolarity and analytes of interest, or the separate detection of osmolarity and analytes of interest. In this particular embodiment, integrated sheath 505 protects the tip of the microfluidic chip, window and detection substrate, and the integrated sheath 505 is pulled off once the device is placed onto a pen-type device and is ready for testing. Blister pack reservoir 506 is protected from user interaction by the capsule (housing), but capsule/housing hole 507 allows a plunger (not shown, as a non-limiting example, a properly sized plunger external to the microfluidic device 50) to burst the blister and provide pressure-driven flow through the microfluidic network within the carrier 508, which couples to the microfluidic osmolarity chip 509 through pressure sensitive adhesive 510. In some embodiments, capsule wings 511 and flanges 512 provide mechanical mating features for the opposing pen, while grip features 513 allow the user to easily grasp and handle the device as a whole.

The aforementioned embodiments allow, in some embodiments, for both osmolarity and other analytes of interest to be quantified on the same platform with a minimum of user interaction. In some embodiments, the microfluidic devices described herein are provided in various different formats so as to facilitate sample collection and readout of measurement results. As a non-limiting example, the microfluidic device is provided as a disposable unit that is used in conjunction with a pen-type device. In some embodiments, the pen device is shaped to receive and couple a microfluidic device. In some embodiments, the pen device validates the microfluidic device and signals to the user the microfluidic device is unused and ready to sample. In some embodiments, the user removes a protective sheath that keeps the sampling tip clean and uses the sampling tip to collect tears from a patient (as a non-limiting example, from a single eye or from both eyes).

In some embodiments, the systems, devices, and methods as disclosed herein include a base unit. In some embodiments, the base unit is reversibly attached to the microfluidic device. In further embodiments, the reversible attachment is one or more selected from: a mechanical attachment, a fluidic communication, and an electrical or electronic communication. In some embodiments, once sample collection is complete, the pen device and coupled microfluidic device are then docked into a base unit (as a non-limiting example, a reader device) that automatically actuates any active valves to enable release and flow of the wash fluid, and then performs the analyte detection assay and/or generates a readout of the recorded sample readings. In other embodiments, once sample collection is complete, the pen device and coupled microfluidic device are then docked into a base unit (as a non-limiting example, a reader device) that automatically lowers a plunger to eventually burst a blister pack, that enables release and flow of a transfer fluid through the microfluidic circuit, and then performs the analyte detection assay and/or generates a readout of the recorded sample readings. In some embodiments, the user removes the microfluidic device from the pen device following tear collection and place the microfluidic device into the base unit, which then automatically performs actuation and displays the sample reading results. In such embodiments, the pen device communicates the recorded osmolarity reading to the base unit (as a non-limiting example, using wireless communication methods) while the base unit carries out the analyte of interest assay. Given the large number of analytes able to be interrogated by this system, in some embodiments, the disposable microfluidic device contains markings, such as a barcode or two-dimensional barcode, that allow the base unit to recognize relevant assay parameters (as a non-limiting example, timing, intensity, excitation wavelengths, emission wavelengths, or number of analytes) and perform the appropriate assay procedures. In alternative embodiments, the microfluidic device itself provides a semi-quantitative or qualitative optical readout of the analytes of interest that is directly read by the user.

In some embodiments, the pen devices include mechanisms to detect and signal to the user once a sufficient volume of tear fluid has been collected (as a non-limiting example, audible signals including beeps or the like, visual signals including lights or the like, haptic signals including vibrations or the like). In some embodiments, the user then removes the disposable microfluidic device, manually presses the blister to release the fluid from the blister, and then docks the microfluidic device into the base unit for analysis.

The systems, devices, and methods as described herein are compatible with a wide variety of assay formats. Non-limiting example of assay includes one or more selected from: an assay based on enzyme-linked immunosorbent assay (ELISA), a sandwich ELISA, a competitive ELISA, a nanoparticle-based detection, a surface plasmon resonance (SPR) based detection, an electrochemical detection, a chromatographic detection, a flow through assays, a lateral flow, and the like. In some embodiments, the microporous substrate serves to capture the wash fluid while the assay reaction is performed within the capillary channel. As a non-limiting example, in certain embodiments, both impedance indicative of osmolarity and a differential impedance measurement are made as nanoparticles accumulate on an interdigitated electrode array inside the capillary channel, as compared to an upstream interdigitated electrode array with nonspecific antibodies attached. In other embodiments, both impedance (osmolarity) and an electrochemical measurement are made within the capillary channel. In alternative embodiments, an impedance measurement indicative of osmolarity is made within the capillary channel and the microporous substrate acts as a lateral flow substrate to allow fluorescent detection.

In some embodiments, the substrates provided herein have geometries shaped to increase flow homogenization over the sample region so to minimize the effects of substrate inhomogeneity (as a non-limiting example, from manufacturing variance, local anisotropies in substrate density), clogging (as a non-limiting example, due to particulate matter and biological crosslinking accumulating within the pores of the substrate), and/or other sources of fluidic anisotropy. In some embodiments, the geometries are designed to generate predetermined regions of increased flow resistance in the detection substrate. By taking advantage of flow resistance in this manner, timed delays, predictable flow expansion, and/or flow contraction is able to be used to ensure that any nanoparticle or biological cross-linking that may otherwise cause clogging and non-uniform wetting of the sample regions are reduced or obviated. In some embodiments, similarly, substrates are operatively shaped to encourage fluid transfer from the capillary channel to at least one specific region of a membrane, while simultaneously encouraging pressure-driven overflow to be wicked away rather than enter the second sample region. In some embodiments, the at least one specific region is the first or the second sample region. In other embodiments, substrates are operatively shaped to allow transfer fluid to preferentially flow downstream prior to reaction components of an ELISA so to hydrate embedded capture antibodies, as small volumes of tear fluid may be insufficient to rehydrate high resistance pillars of antibody within a nitrocellulose membrane by the time the bolus of tear has flowed past the first sample region.

Figure 6G:
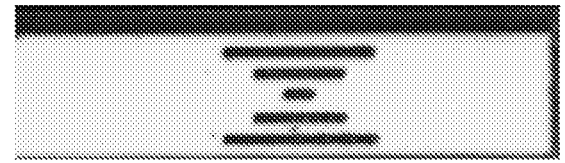
FIGS. 6A through 6G illustrate non-limiting exemplary detection substrates with geometries for achieving flow homogenization, in accordance with some embodiments.
Figure 6F:
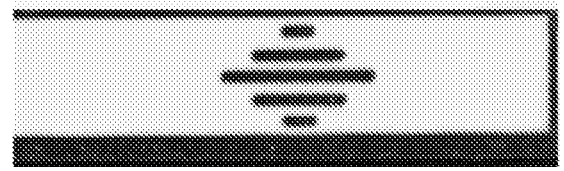
Figure 6E:
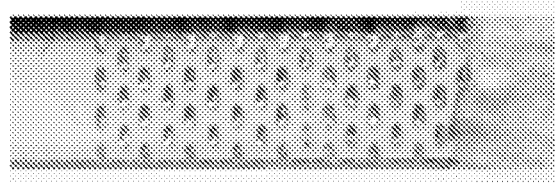
Figure 6D:
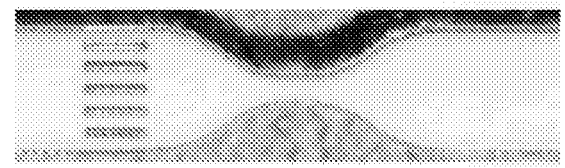
Figure 6C:
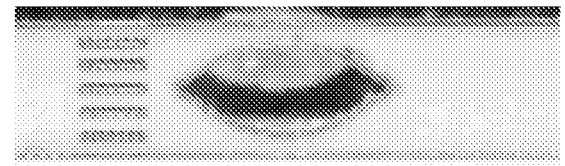
Figure 6B:
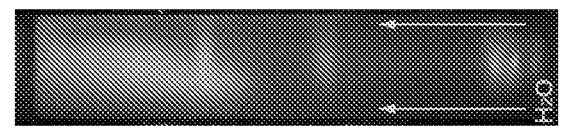
Figure 6A:

FIGS. 6A through 6E illustrate exemplary detection substrates with geometries for achieving a substantially isotropic (uniform) fluid front as the fluid traverses the second sample region in the direction of flow, in accordance with many embodiments. FIGS. 6F through 6G show non-limiting examples of inhomogeneous, anisotropic nanoparticle downstream distributions as a direct result of the initial conditions of the upstream nanoparticle distribution and the resulting unmodified flow. Specifically, FIG. 6F shows how nanoparticles spotted in the center line (at the bottom of the figure) flow vertically upwards while being focused into a central trail by the faster moving fluid that prevents nanoparticles from reaching the edges of the striped capture region. FIG. 6G shows the opposite example, where nanoparticles spotted across the width of the strip are pushed to the edges, resulting in a signal only at the outer edges of the striped capture region. Accordingly, FIG. 6A shows a pattern that focuses flow towards the middle as there is less resistance than on the long edges of the pattern, which is useful for when detection nanoparticles striped across the entire width of membrane: since nanoparticles add resistance to the fluid path, an upstream stripe of horizontal nanoparticle tends to have fluid preferentially flow down the middle and deposit the nanoparticles at the far edges of the strip, thus, focusing the flow down the middle helps create a more uniform flow profile. FIG. 6B demonstrates a particular embodiment of a design useful for pushing fluid towards the edges, to compensate for when nanoparticles are spotted (or are transferred onto the membrane) down the middle. FIGS. 6C through 6D show non-limiting examples of different type of flow control structures including constrictions, expansions and downstream resistors that make flow more uniform by changing cross-sectional resistance. In addition, these structures of FIGS. 6C-D feature downstream resistance that helps balance and prevent random instabilities from shifting the flow from one side of the membrane to the other. These approaches are quite important when analyzing small sample volumes as the sample flow front may not permit uniform transport of detectable moieties across the fluid channel or a detection zone without guidance, as many times, the detectable moieties introduce a resistance that changes with time and space as the sample flows across the membrane, especially if the detectable moieties use nanoparticles as labels.

With regard to FIGS. 6A through 6E, in some embodiments, the detection substrates are microporous membranes or microporous substrates, as discussed above. In some embodiments, the substrates include one or more geometries designed to produce flow restrictions. Such geometries are fabricated by various methods, as non-limiting examples, punching, heating, branding, wax deposition, antibody or other protein deposition, covalent attachment of high resistance polymers or inorganic compounds, or laser patterning. In the depiction of FIGS. 6A through 6E, the fluid flow is designed to cause the sample volume to migrate through the substrate (from bottom to top) so as to take advantage of entrance region effects and flow expansions after a restriction to increase flow homogenization. For instance, the substrate of FIG. 6A includes a series of a parallel elongated apertures near the middle of the substrate. The lengths of the apertures decrease when moving from the edges of the substrate to the center. The substrate of FIG. 6B is similar to that of FIG. 6A, except that the lengths of the apertures increase when moving from the edges of the substrate to the center. The substrate of FIG. 6C includes a plurality of small openings arranged in a grid pattern. The substrate of FIG. 6D is formed in an hourglass shape, such that the central portion of the substrate is significantly narrower than the ends. The substrate of FIG. 6E includes an oval-shaped aperture in the center portion, such that the upper end of the substrate is joined to the lower end of the substrate by two relatively narrow strips of material.

Certain embodiments provided herein also lend themselves to flow focusing to allow parallel sample regions within each membrane. The embodiments of FIGS. 6D and 6E include a series of parallel channels in the upper portion of the substrate that are amenable to parallel sample processing. In some embodiments, these channels are designed to take advantage of the increased flow homogenization that occurs after the sample volume passes from the restricted regions to the expanded regions of the substrate.

In some embodiments, the fluid volumes used are extremely small, as discussed above. In further embodiments, the fluid volumes include one or more selected from: a sample fluid volume, a wash fluid volume, and a transfer fluid volume. Accordingly, in various embodiments, one or more additional features are integrated into the capillary channel and/or detection substrate to control flow and accurately meter the sample. A non-limiting example of such a feature is high spatial frequency changes in surface energy within the capillary channel, which are known to act as speed bumps that change the shape of the receding meniscus during evaporation, effectively slows the movement of the fluidic volume. Similarly, in some embodiments, serpentine channels or other delays are patterned into the detection substrate to modulate assay timing and improve assay sensitivity (as a non-limiting example, slower flow results in longer reaction times over sample regions).

Figure 7:
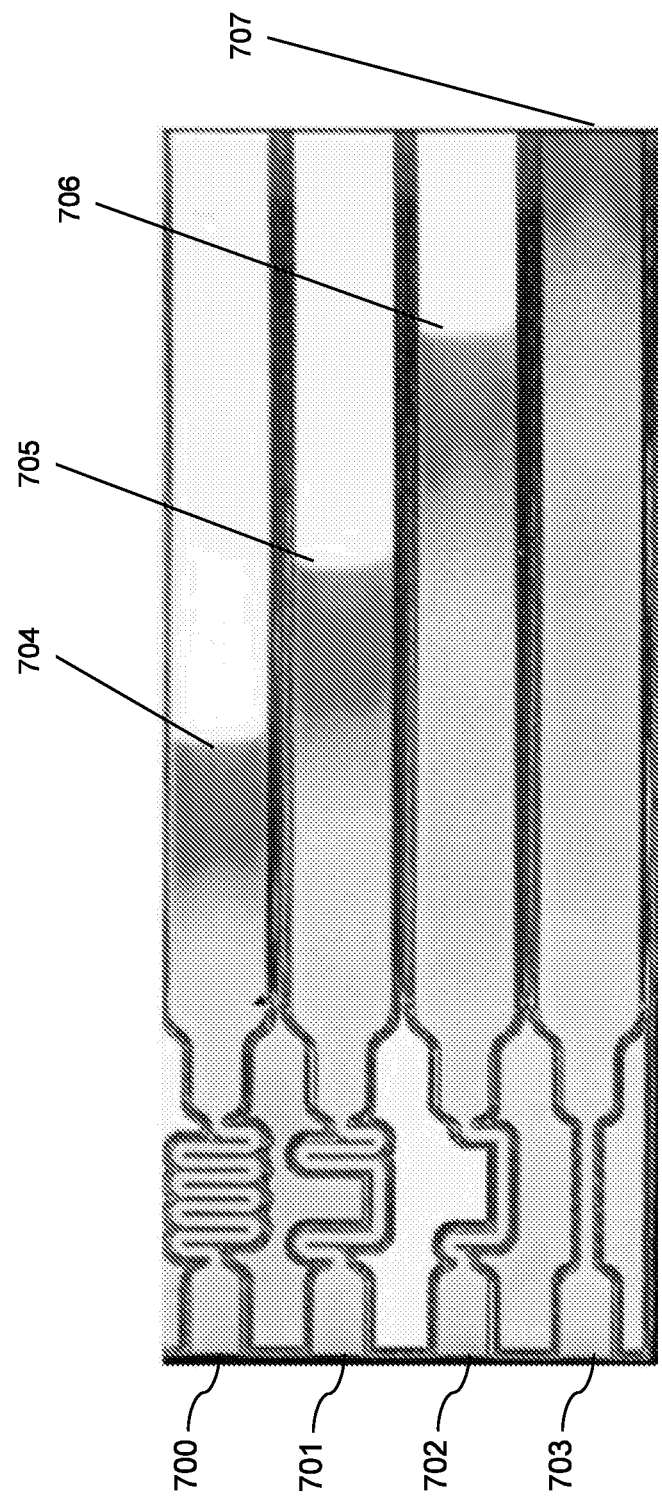
FIG. 7 illustrates non-limiting exemplary detection substrates configured to effect precision fluid timing delays, in accordance with some embodiments.

In a particular embodiment, FIG. 7 illustrates embodiments of detection substrate patterns that effect fluidic timing delays, in accordance with many embodiments. In some embodiments, the detection substrates are microporous membranes or microporous substrates, as discussed above. In some embodiments, the geometries of the detection substrates are designed to influence the length of the timing delay, thereby providing control over various assay parameters. For instance, substrates 700, 701, 702, and 703 exhibit decreasing amounts of serpentine channel structures, with substrate 700 having the most serpentine structures and substrate 703 having no serpentine structures. The amount of serpentine structures in the substrate influences the amount by which fluid flow through the substrate is delayed, as evidenced by the different extents to which the dye fronts 704, 705, 706, 707 have progressed across their respective substrates 700, 701, 702, and 703. Notably, the highly serpentine substrate 700 exhibits the largest time delay of fluid flow, whereas the linear substrate 703 exhibits the least delay of fluid flow.

Figure 8:
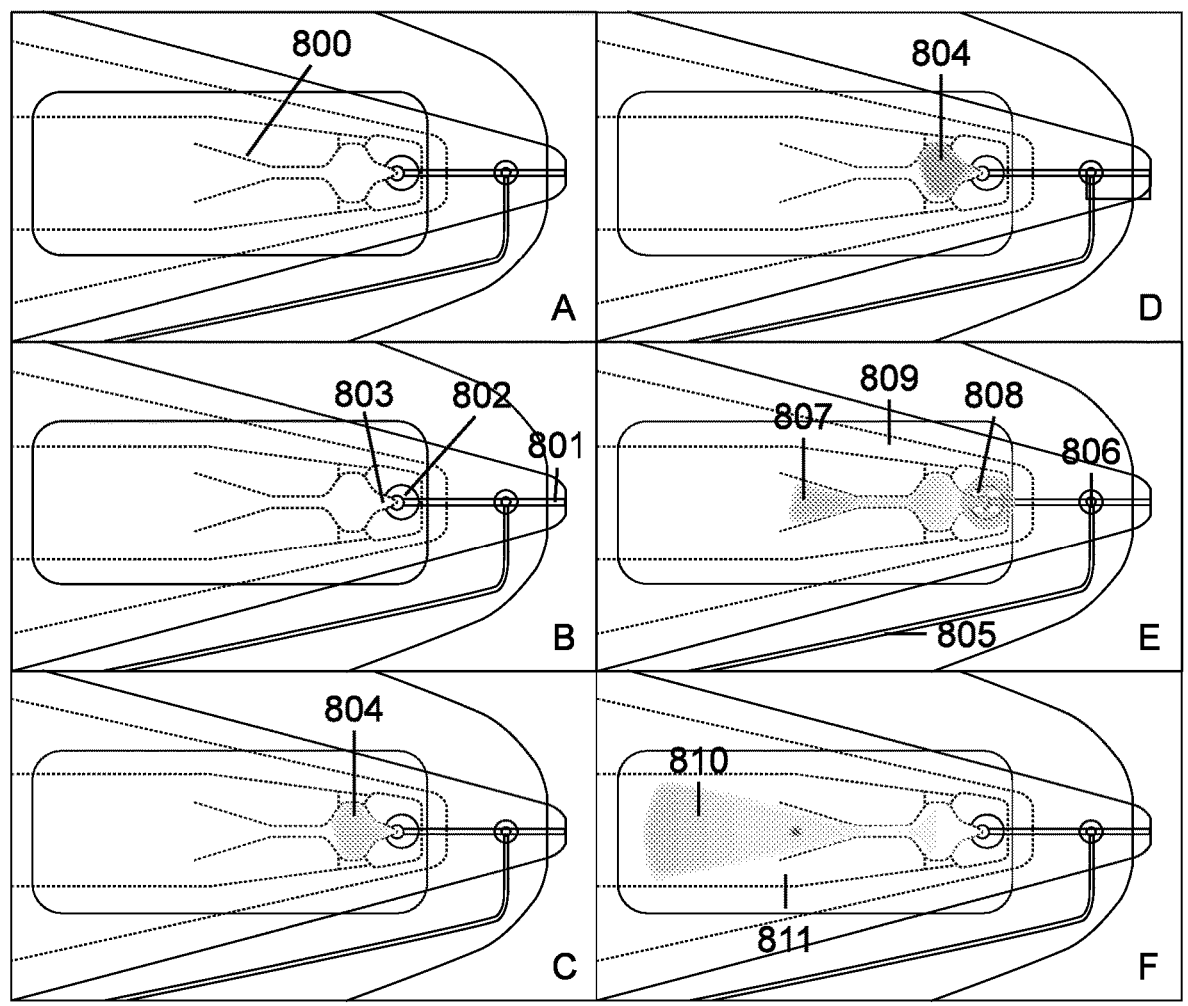
FIG. 8 shows a non-limiting illustration of a serially measured osmolarity and 250 ng/mL IgE using approximately 100 nL of human tear fluid.

In a particular embodiment, FIG. 8 illustrates a preferred embodiment of a microporous nitrocellulose polymer 800 (dashed line) bonded to a polycarbonate microfluidic chip with integrated impedance electrodes. In this embodiment, upon collection of nanoliters of tear fluid at the tip, tear fluid is first analyzed for tear osmolarity as shown in FIG. 8A. In the same embodiment, subsequent actuation of a blister pack reservoir via a computer controlled, stepper motor driven plunger (not shown) creates an air pulse that pushes the tear from the collection channel 801 past the passive valve 802 (vent valve), onto the microporous nitrocellulose membrane, which is patterned with a tongue structure 803 (that descends substantially into the top of the passive valve 802) as shown in FIG. 8B. FIG. 8C shows the tear sample 804 fully wicked onto of the microporous membrane following initial blister reservoir actuation, but prior to bursting. In this particular embodiment, while waiting for blister burst and running buffer flow to drive the assay in FIG. 8D, the tear sample incubates with the detector complex comprising antibody functionalized fluorescent Europium chelate nanoparticles (shown under ultraviolet (UV) illumination with a red, long-pass filter). Following blister rupture, buffer travels through microchannel 805, down across tip valve 806, back through channel 801, up through vent valve 802, onto tongue 803, thereby triggering flow of the reacted nanoparticle/tear complex over the second sample region 807, as shown in FIG. 8E. In this embodiment, the buffer accumulates atop the vent valve and tongue while supplying the lateral flow reaction, creating a dome of fluid 808, illustrated by the lensed reflection of the four illumination lights. In this embodiment, the microporous substrate is patterned with overflow channels 809, adjacent to valve 802. In some embodiments, overflow channels 809 help mitigate the risk of the dome of fluid building and cresting over the lateral flow assay, which provides a short circuit path for fluid to move over the membrane rather than through the membrane. FIG. 8F shows the result of completed assay in which the initial bolus of reacted nanoparticle/tear complex 810 has spread out to match the contour of the microporous membrane structure. In some embodiments, the thickness of bolus 810 is controlled by the initial concentration, distribution, charge density, crosslinking status and volume of the nanoparticles spotted onto the microporous membrane. In some embodiments, by configuring the second sample region to interrogate only a subset of the total volume available, the assay makes the intensity of spot 811 relatively volume independent. In some embodiments, within assay linearity limits, the higher the concentration of analyte in tear, the higher the intensity of spot 811, and the lower the concentration, the lower the intensity.

Figure 9:
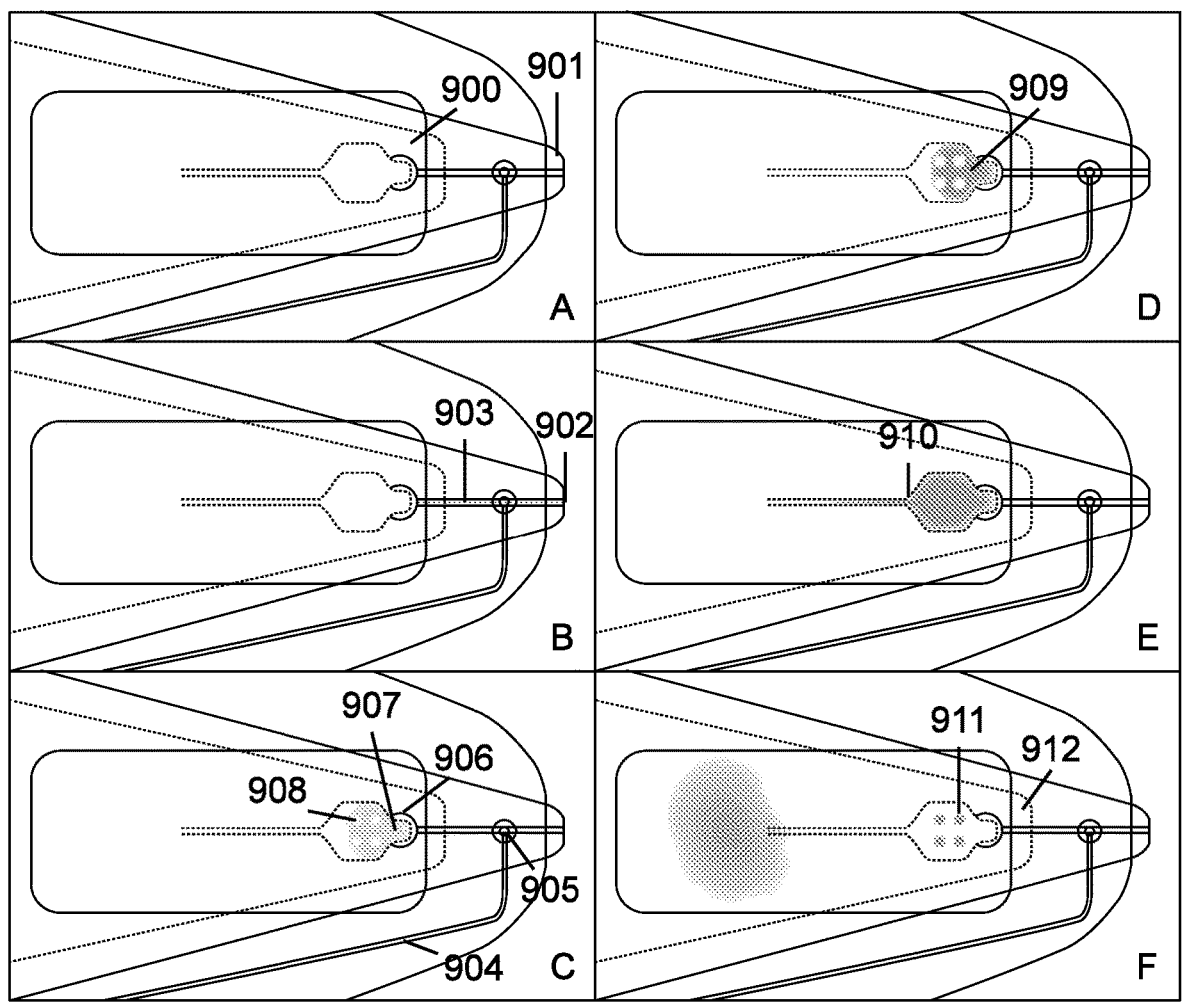
FIG. 9 shows a non-limiting illustration of a multiplexed assay within a rehydration structure containing segregated rehydration channels.

FIG. 9 illustrates a preferred embodiment of a nitrocellulose polymer 900 (dashed line) bonded to a polycarbonate microfluidic chip 901 with integrated impedance electrodes as shown in FIG. 9A. Upon collection of nanoliters tear fluid at the leftmost tip 902, tear fluid is first analyzed for tear osmolarity in while in channel 903 in FIG. 9B. Subsequent actuation of a blister pack reservoir via a computer controlled, stepper motor driven plunger (not shown) creates an air pulse that travels down channel 904, through tip valve 905, pushes the tear from past the passive vent valve 906, and onto the microporous membrane, which is patterned with a tongue structure 907 (that is pressed substantially into the top of the vent valve by a polycarbonate finger protrusion emanating down from the top of the carrier plastic housing (not shown), resulting in the initial sample transfer as shown in FIG. 9C. In this particular embodiment shown in FIG. 9, antibody functionalized Eu chelated nanoparticles are included in the vent valve 906 prior to running the assay, rather than on the nitrocellulose membrane, allowing the tear and nanoparticles to incubate while in the collection channel. As evidenced in FIG. 9C, multiplexed, spotted capture antibodies 908 creates a fluidic resistance that prevents small nanoliter volumes of fluid from effectively rehydrating the sample region. This is also seen in FIG. 9D under red filtered UV illumination, where the glow of the nanoparticles 909 is effectively excluded from the capture antibody spots. Since the entirety of the analyte of interest signal is contained within the initial bolus of fluid, downstream fluidic constriction 910 creates an increase in downstream resistance that causes the sample fluid to preferentially flow through the capture spots rather than around the capture spots, as the capture spots are now lower resistance than through the center of the channel, facilitating the chromatographic assay where the nanoparticles flow over the capture antibody, as shown in FIG. 9E. A multiplexed result 911 is seen in FIG. 9F, as a result of the sandwich immunoassay capturing a series of detection complex-bound analytes of interest within the sample fluid as it flowed past. In addition, overflow channels 912 surrounding the assay channel take up excess fluid to prevent a dome of buffer from flowing over the top of the microporous substrate and giving the running buffer a path of least resistance other than through the second sample region.

In some embodiments, two elements selected from the following are in fluid communication with each other: a capillary channel, a detection substrate, a microporous substrate, a capsule, a capillary chip, a cavity defined by an interior wall of a capsule, a reservoir, a passage fluidically connected to the detection substrate, a valve, a vertical inlet, and an inlet.

In some embodiments, the systems, devices, and methods as disclosed herein include a blister pack or use of the same. In some embodiments, the blister pack includes at least one enclosed and sealed volume configured to hold a fluidic volume therewithin. In some embodiments, the fluidic volume enclosed within the blister pack is released in a predetermined manner when an actuating element is applied to the blister pack. In some embodiments, the actuating element is external to or within the devices, systems as disclosed herein. In some embodiments, the fluidic volume within the blister is sufficient to wash the first sample region, the second sample region, or one or more of elements within the device or system as disclosed herein. In some embodiments, the fluidic volume within the blister is sufficient to transfer sample fluid to the first sample region, the second sample region, or one or more of elements within the device or system as disclosed herein so that the system or device generates a valid first sample reading or a valid second sample reading based on the sample fluid transferred thereby. In some embodiments, the fluidic volume within the blister is within a range from about 10 nL to about 50 µL, or within a range from about 50 nL to 500 nL. In some embodiments, the fluidic volume is within a range between any two of the following: about 10 nL, about 20 nL, about 30 nL, about 40 nL, about 50 nL, about 60 nL, about 70 nL, about 80 nL, about 90 nL, about 100 nL, about 150 nL, about 200 nL, about 250 nL, about 300 nL, about 400 nL, about 500 nL, about 600 nL, about 700 nL, about 800 nL, about 900 nL, about 1 µL, about 2 µL, about 3 µL, about 4 µL, about 5 µL, about 6 µL, about 7 µL, about 8 µL, about 9 µL, about 10 µL, about 11 µL, about 12 µL, about 13 µL, about 14 µL, about 15 µL, about 16 µL, about 17 µL, about 18 µL, about 19 µL, about 20 µL, about 21 µL, about 22 µL, about 23 µL, about 24 µL, about 25 µL, about 26 µL, about 27 µL, about 28 µL, about 29 µL, about 30 µL, about 31 µL, about 32 µL, about 33 µL, about 34 µL, about 35 µL, about 36 µL, about 37 µL, about 38 µL, about 39 µL, about 40 µL, about 41 µL, about 42 µL, about 43 µL, about 44 µL, about 45 µL, about 46 µL, about 47 µL, about 48 µL, about 49 µL, or about 50 µL. In some embodiments, the fluidic volume is no more than about 20 µL, about 250 nL, about 200 nL, or about 50 nL. The fluidic volume is no more than about 10 nL, about 20 nL, about 30 nL, about 40 nL, about 50 nL, about 60 nL, about 70 nL, about 80 nL, about 90 nL, about 100 nL, about 150 nL, about 200 nL, about 250 nL, about 300 nL, about 400 nL, about 500 nL, about 600 nL, about 700 nL, about 800 nL, about 900 nL, about 1 µL, about 2 µL, about 3 µL, about 4 µL, about 5 µL, about 6 µL, about 7 µL, about 8 µL, about 9 µL, about 10 µL, about 11 µL, about 12 µL, about 13 µL, about 14 µL, about 15 µL, about 16 µL, about 17 µL, about 18 µL, about 19 µL, about 20 µL, about 21 µL, about 22 µL, about 23 µL, about 24 µL, about 25 µL, about 26 µL, about 27 µL, about 28 µL, about 29 µL, about 30 µL, about 31 µL, about 32 µL, about 33 µL, about 34 µL, about 35 µL, about 36 µL, about 37 µL, about 38 µL, about 39 µL, about 40 µL, about 41 µL, about 42 µL, about 43 µL, about 44 µL, about 45 µL, about 46 µL, about 47 µL, about 48 µL, about 49 µL, or about 50 µL.

In some embodiments, the system, devices, and methods as disclosed herein include an interface. In further embodiments, the interface is located between the first and the second sample regions. In even further embodiments, the interface is configured to minimize the amount of bare membrane that the sample fluid interacts with. In some embodiments, the interface is shaped and located in order to minimize the amount of bare membrane that the sample fluid interacts with.

Accordingly, in some embodiments, the present disclosure provides systems, methods, and devices that facilitate integration of microfluidic tear collection and biological assays of analytes of interest into a single receiving device. Various embodiments of the integrated device described herein allow for nanoliter-scale tear collection, accurate metering of tear fluid, a fluidic movement delay to facilitate tear osmolarity measurement, incubation of tears with detection conjugates, timed transfer of nanoliters of fluid to the sample region, and/or features to enable a blister-actuated wash and optical quantification of a plurality of analytes of interest. In some embodiments, the results of such analyses are applied to the treatment and monitoring of a wide variety of eye conditions, such as dry eye disease, glaucoma, diabetic retinopathy, allergy, keratoconus, macular degeneration, or other eye diseases. As a non-limiting example, the sample readings generated using the approaches described herein are used as a basis for adjusting treatment planning for various eye conditions.

As used herein A and/or B encompasses one or more of A or B, and combinations thereof such as A and B.

Where a range of values is provided, it is understood that each intervening value, to the tenth of the unit of the lower limit unless the context clearly dictates otherwise, between the upper and lower limit of that range, and any other stated or intervening value in that stated range, is encompassed within the disclosure provided herein. In some embodiments, the upper and lower limits of these smaller ranges are independently be included in the smaller ranges, and are also encompassed within the disclosure, subject to any specifically excluded limit in the stated range. Where the stated range includes one or both of the limits, ranges excluding either or both of those included limits are also included in the disclosure provided herein.

In some embodiments, ranges are expressed herein as from "about" one particular value, and/or to "about" another particular value. When such a range is expressed, another embodiment includes from the one particular value and/or to the other particular value. Similarly, when values are expressed as approximations, by use of the antecedent "about," it will be understood that the particular value forms another embodiment. It will be further understood that the endpoints of each of the ranges are significant both in relation to the other endpoint, and independently of the other endpoint. The term "about" as used herein refers to a range that is 10% plus or minus from a stated numerical value within the context of the particular usage.

Unless otherwise specified, the presently described methods and processes are performed in any order. As a non-limiting example, a method describing steps (a), (b), and (c) is performed, in some embodiments with step (a) first, followed by step (b), and then step (c). Or, in some embodiments, the method is performed in a different order such as, as a non-limiting example, with step (b) first followed by step (c) and then step (a). Furthermore, in some embodiments, those steps are performed simultaneously or separately unless otherwise specified with particularity.

The specific dimensions of any of the apparatuses, devices, systems, and components thereof, of the present disclosure can be readily varied depending upon the intended application, as will be apparent to those of skill in the art in view of the disclosure herein. Moreover, it is understood that the examples and embodiments described herein are for illustrative purposes only and that various modifications or changes in light thereof can be suggested to persons skilled in the art and are included within the spirit and purview of this application and scope of the appended claims. Numerous different combinations of embodiments described herein are possible, and such combinations are considered part of the present disclosure. In addition, all features discussed in connection with any one embodiment herein can be readily adapted for use in other embodiments herein. The use of different terms or reference numerals for similar features in different embodiments does not necessarily imply differences other than those expressly set forth.

Unless otherwise defined, all technical terms used herein have the same meaning as commonly understood by one of ordinary skill in the art to which this invention belongs. As used in this specification and the appended claims, the singular forms "a," "an," and "the" include plural references unless the context clearly dictates otherwise. Any reference to "or" herein is intended to encompass "and/or" unless otherwise stated. As used in this specification and the claims, unless otherwise stated, the term "about" or the term "approximately" refers to variations of +/−1%, +/−2%, +/−3%, +/−4%, +/−5%, +/−6%, +/−7%, +/−8%, +/−9%, +/−10%, +/−11%, +/−12%, +/−14%, +/−15%, +/−16%, +/−17%, +/−18%, +/−19%, +/−20%, +/−22%, or +/−25%, depending on the embodiment. As a non-limiting example, about 100 meter represents a range of 95 meters to 105 meters, 90 meters to 110 meters, or 85 meters to 115 meters depending on the embodiments.

Example 1

This example describes the operation of a device capable of measuring both the osmolarity and the amount of an analyte of interest in a small volume of a fluid sample.

The device was constructed and operated as discussed hereinabove in connection with FIGS. 8 and 9. As exemplified in FIG. 8, approximately 150 nL human tear spiked with 250 ng/mL IgE was applied to the fluid inlet of an assembled device. The assembled device wicked fluid into the capillary tube while interrogating the impedance and temperature of the sample. Introduction of the sample caused a sharp reduction in impedance that triggered a computer program to begin to lower a plunger to burst the blister pack reservoir disposed within the capsule/housing of the assembled device. Once the blister burst and transfer fluid traveled through the system, a spot of 36 pixels in diameter appeared with a mean 8-bit intensity of 52.74, while the upstream background mean of an identical spot showed 28.14 and downstream 20.23, resulting in a final signal of 52.74−((28.14+20.23)/2)=28.56 from the red channel. An equivalent setup using 100 ng/mL spiked IgE resulted in a spot intensity of 34.12, an upstream background mean of 28.88 and a downstream intensity of 21.71, resulting in a final signal of 34.12−((28.88+21.71)/2)=8.83, while a healthy, unspiked control tear sample resulted in a spot intensity of 21.91, an upstream background of 23.46, and downstream background of 19.03, resulting in a final signal of 21.91−((23.46+19.03)/2)=0.67. The signal-to-noise ratio of the 250 ng/mL was 42.3, while the signal-to-noise ratio of the 100 ng/mL sample was 13.2. This experiment demonstrated the detection and quantification of analytes of interest in very small sample volumes. Although the device was capable of also measuring osmolarity, it is contemplated that devices can be configured to measure the presence and/or amount of one or more analytes of interest in a test sample.

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

The entire disclosure of each of the patent documents and scientific articles referred to herein is incorporated by reference for all purposes.

The invention may be embodied in other specific forms without departing from the spirit or essential characteristics thereof. The foregoing embodiments are therefore to be considered in all respects illustrative rather than limiting the invention described herein. Scope of the invention is thus indicated by the appended claims rather than by the foregoing description, and all changes that come within the meaning and range of equivalency of the claims are intended to be embraced therein.

What is claimed is:

1. A device for analyzing a fluidic sample, the device comprising:
   (a) a fluid inlet;
   (b) a first sample region in fluid communication with the fluid inlet, wherein the first sample region comprises at least one transducer configured to detect an energy property of the fluidic sample and generate a first sample reading, wherein the first sample reading is indicative of osmolarity of the fluidic sample;
   (c) a second sample region in fluidic communication with the first sample region and shaped to receive a volume of 10 nL to 500 nL of the fluidic sample, the second sample region comprising a detection substrate configured to permit detection of one or more analytes in the volume of the fluidic sample to generate a second sample reading;
   (d) a first valve disposed between the first sample region and the second sample region, wherein the first valve controls fluid flow between the first sample region and the second sample region, wherein at least a portion of the detection substrate is positioned substantially into a first end of the first valve and spaced apart from the first sample region;
   (e) a fluid reservoir disposed within the device and in fluidic communication with the second sample region, the fluid reservoir containing a transfer fluid, which when transferred to the second sample region is capable of hydrating a reagent disposed within the second sample region, washing the detection substrate during operation of the device, or both; and
   (f) a second valve disposed between the fluid reservoir and the second sample region.

2. The device of claim 1, wherein the detection substrate comprises a microporous substrate comprising one or more serpentine channels that act as a fluidic delay and a path for sample transfer, and, during operation, at least a portion of the volume traverses the microporous substrate.

3. The device of claim 1, wherein the detection substrate comprises a microporous substrate having one or more flow control structures to adjust a direction of flow of the volume of fluidic sample as it traverses the second sample region.

4. The device of claim 2, wherein the microporous substrate comprises a plurality of apertures to facilitate a substantially uniform fluid front.

5. The device of claim 1, wherein the detection substrate further comprises an immobilized first binder capable of binding, either directly or indirectly, the one or more analytes if present in the volume.

6. The device of claim 5, wherein the detection substrate further comprises a second binder capable of binding the one or more analytes if present in the volume, wherein the second binder optionally is conjugated with a detectable moiety.

7. The device of claim 1, wherein the fluid inlet is adjacent and oriented perpendicular to a flow of the fluidic sample from a sample tip shaped to receive a volume of the fluidic sample.

8. The device of claim 1, wherein the reservoir is disposed on a carrier comprising a microfluidic reservoir to delay flow or trap bubbles.

9. The device of claim 1, wherein the first sample region and the second sample region are fluidically coupled via a through-hole or passage.

10. The device of claim 2, wherein the microporous substrate further comprises overflow channels adjacent to the valve.

11. The device of claim 2, wherein the microporous substrate further comprises shorter path length rehydration channels.

12. The device of claim 11, wherein the shorter path length rehydration channels surround a central path for sample transfer.

13. The device of claim 1, wherein the fluid reservoir is partitioned to hold more than one of a transfer buffer, wash fluid, transfer fluid, sample fluid, gas, or air.

14. The device of claim 1, further comprising a plunger that creates an air pulse to push the volume past the first valve.

15. The device of claim 1, wherein the energy property of the fluidic sample is an impedance of the fluidic sample.

16. The device of claim 1, wherein the at least a portion of the detection substrate comprises a tongue configuration that descends into the first end of the first valve.

17. The device of claim 1, wherein the at least a portion of the detection substrate descends from the second sample region into the first end of the first valve.

18. The device of claim 1, further comprising a plurality of electrodes disposed within and/or adjacent to the first sample region and configured to determine when a prescribed amount of volume of the fluid sample is collected within the first sample region.

19. The device of claim 1, wherein the second valve is disposed between the fluid reservoir and the first sample region.

20. The device of claim 1, wherein the first valve is oriented perpendicular to a flow of the fluidic sample from the first sample region.

* * * * *